US012336885B2

(12) United States Patent
Smith

(10) Patent No.: US 12,336,885 B2
(45) Date of Patent: Jun. 24, 2025

(54) CUSTOMIZABLE HEARING PROTECTION DEVICES WITH INTERCHANGEABLE INSERTS AND ACCESSORIES

(71) Applicant: You Tune Hearing Protection LLC, Dayton, OH (US)

(72) Inventor: Jeremiah Smith, Dayton, OH (US)

(73) Assignee: YOU TUNE HEARING PROTECTION LLC, Dayton, OH (US)

( * ) Notice: Subject to any disclaimer, the term of this patent is extended or adjusted under 35 U.S.C. 154(b) by 563 days.

(21) Appl. No.: 17/590,306

(22) Filed: Feb. 1, 2022

(65) Prior Publication Data
US 2022/0151833 A1    May 19, 2022

Related U.S. Application Data

(63) Continuation-in-part of application No. 16/050,971, filed on Jul. 31, 2018, now abandoned.

(60) Provisional application No. 62/539,182, filed on Jul. 31, 2017.

(51) Int. Cl.
*A61F 11/08* (2006.01)
*G10K 11/16* (2006.01)

(52) U.S. Cl.
CPC ............ *A61F 11/085* (2022.01); *G10K 11/16* (2013.01)

(58) Field of Classification Search
CPC .......... A61F 11/08; A61F 11/06; A61F 11/10; A61F 2011/085; H04R 1/1016; H04R 25/02; G10K 11/16
See application file for complete search history.

(56) References Cited

U.S. PATENT DOCUMENTS

| | | | |
|---|---|---|---|
| 2,521,414 A | 9/1950 | Schier | |
| 4,540,063 A | 9/1985 | Ochi et al. | |
| 5,332,871 A * | 7/1994 | Carrigan | A61F 11/08 181/135 |
| 6,082,485 A * | 7/2000 | Smith | A61F 11/08 128/868 |
| 6,148,821 A | 11/2000 | Falco | |
| 6,286,622 B1 * | 9/2001 | Tiemann | A61F 11/08 181/135 |
| 7,182,087 B1 | 2/2007 | Marsh | |
| 7,512,243 B2 | 3/2009 | Haussmann | |

(Continued)

FOREIGN PATENT DOCUMENTS

| | | |
|---|---|---|
| EP | 0 333 298 B1 | 6/1993 |
| EP | 1 795 160 B1 | 5/2009 |

*Primary Examiner* — Camtu T Nguyen
(74) *Attorney, Agent, or Firm* — DINSMORE & SHOHL LLP

(57) ABSTRACT

Customizable hearing protection devices include a body portion. A channel is defined through the body portion. A sound modifying insert is removably inserted into an outer portion of the channel. An adapter insert is removably inserted into an inner portion of the channel. The devices further include an eartip mounted to a mounting portion of the adapter insert that protrudes from the proximal side of the body portion. The channel includes a middle portion connecting the outer portion and the inner portion. The body portion may further include a loop portion, into which an interchangeable chip may be removably inserted. The interchangeable chip may have an outward facing surface with customized indicia thereon.

20 Claims, 26 Drawing Sheets

(56) References Cited

U.S. PATENT DOCUMENTS

| | | |
|---|---|---|
| 7,793,662 B2 | 9/2010 | Elliott |
| 7,889,883 B2 | 2/2011 | Cartwright et al. |
| 8,113,207 B2 | 2/2012 | Gehling et al. |
| 8,931,489 B2 | 1/2015 | Smith |
| 9,282,390 B1 * | 3/2016 | Turdjian ............... H04R 1/1016 |
| 9,333,116 B2 * | 5/2016 | Bauman ................... H03G 3/04 |
| 2013/0259286 A1 * | 10/2013 | Chung ................. H04R 1/1016 |
| | | 381/380 |
| 2014/0190494 A1 * | 7/2014 | Ely ........................ A61F 11/08 |
| | | 128/868 |

* cited by examiner

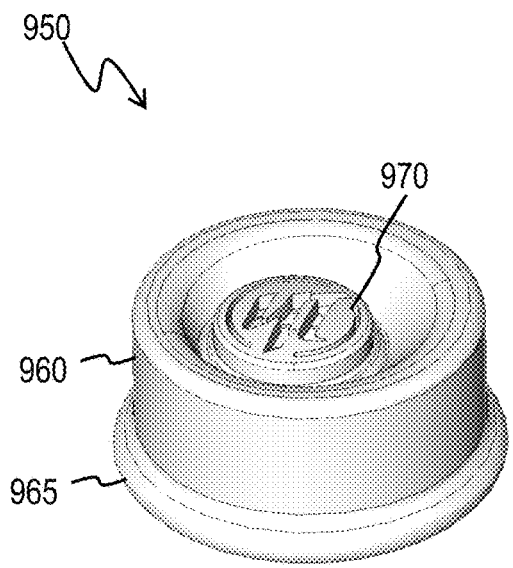
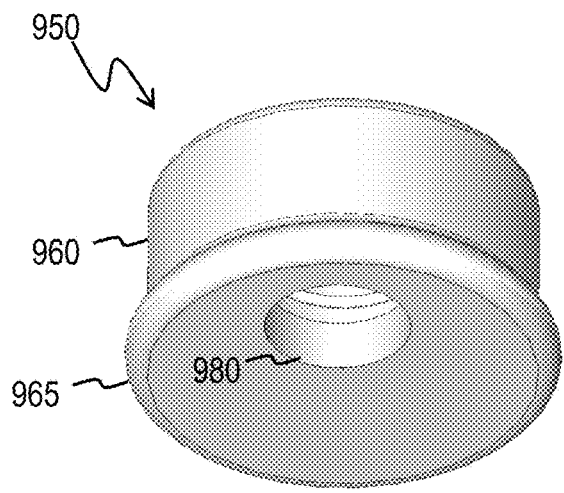
FIG. 21A
FIG. 21B
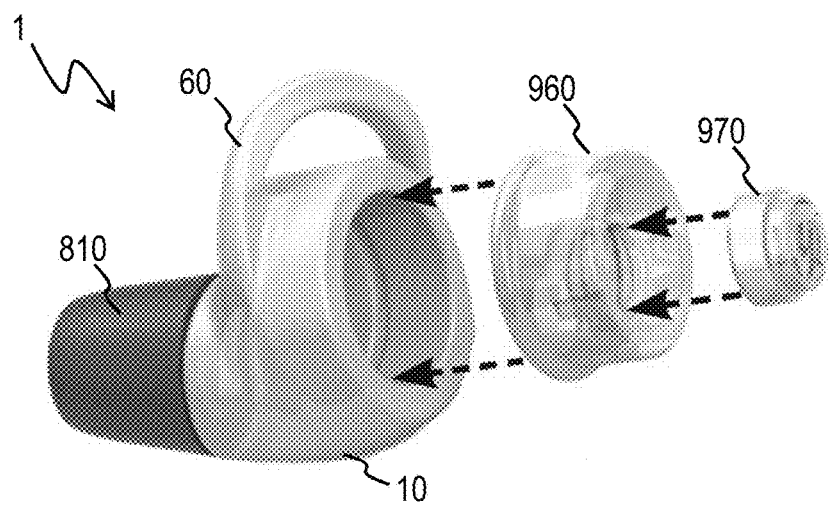
FIG. 22

CUSTOMIZABLE HEARING PROTECTION DEVICES WITH INTERCHANGEABLE INSERTS AND ACCESSORIES

CROSS-REFERENCES TO RELATED APPLICATIONS

This application is a continuation-in-part of U.S. patent application Ser. No. 16/050,971, filed Jul. 31, 2018, which claims benefit of priority to U.S. Provisional Application Ser. No. 62/539,182, filed Jul. 31, 2017. The entire contents of applications 16/050,971 and 62/539,182 are hereby incorporated by reference into this disclosure.

TECHNICAL FIELD

The present disclosure relates to hearing protection devices and, more particularly to multi-application, customizable hearing protection devices and interchangeable inserts and accessories for use with the hearing protection devices.

BACKGROUND

Prolonged or repeated exposure to loud noises or high volume of sound is the leading cause of hearing loss. The amount of hearing loss is preventable when proper ear protection is available and used. Common devices such as earplugs that can be inserted into the ear canal or ear muffs that are worn over the ears may be effective at lowering exposures to loud noises. Nevertheless, such devices must be removed to enable the user to hear voices in their environment after loud noises cease, thereby causing inconvenience or risk that the device will be inaccessible when the loud noises resume. Common devices also tend to muffle or distort sounds in certain frequency ranges, for example, at a loud concert. In such instances, the user's goal may be to simply reduce sound volumes to prevent injury, without a desire for disproportionately losing volume in the middle or high frequency ranges.

Further, crowds of people gathered in one place, for example, as a shooting team, a concert audience, or a pit crew, may have morale benefits from some kind of common identification or attachment to a brand. Particularly when the people so gathered also share a common need for hearing protection, practical and highly visible means of displaying the common identification can help develop a sense of camaraderie in the crowd or can be capitalized upon as an advertising opportunity for the brand. Further, there is virtually no carryover with similar ear related devices, thus earplug use is limited to noisy environments. Noise reduction filters, customizable aesthetic inserts, and electronic accessories could create an obvious queue for use to rebuild prior habits while improving proper ear protection behavior.

There remain ongoing needs for hearing protection devices that are both convenient and effective at lowering the volume of ambient sounds to safe levels, while also being adaptable to preserve the ability to reduce sound volume without decreasing sound quality. There remain further ongoing needs for personalizing and customizing hearing protection devices to supplement dated Hearing Protection Devices (HPD) and create habits with new routines.

SUMMARY

Example embodiments disclosed herein are directed to customizable hearing protection devices. The customizable hearing protection devices include a body portion. A channel is defined through the body portion from a distal side of the body portion to a proximal side of the body portion opposite the distal side. The devices further include a sound modifying insert removably inserted into an outer portion of the channel adjacent to the distal side of the body portion, the outer portion having a first diameter. The devices further include an adapter insert removably inserted into an inner portion of the channel adjacent to the proximal side of the body portion, the inner portion having a second diameter, the second diameter being less than the first diameter. The devices further include an eartip mounted to a mounting portion of the adapter insert that protrudes from the proximal side of the body portion. The channel includes a middle portion connecting the outer portion and the inner portion. The middle portion has a third diameter, the third diameter being less than the second diameter. The adapter insert has a sound path defined through the adapter insert.

Further embodiments are directed to kits for assembling customizable hearing protection devices. The kits include at least one body portion; a sound modifying insert selected from an adjustable noise-reduction attachment, a speaker, a high-fidelity music/impulse cartridge insert, or a combination thereof; at least one adapter insert; and at least one eartip.

These and other features, aspects, and advantages will become better understood with reference to the following description and the appended claims.

Additional features and advantages of the embodiments described herein will be set forth in the detailed description that follows, and in part will be readily apparent to those skilled in the art from that description or recognized by practicing the embodiments described herein, including the detailed description that follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

FIGS. 21A and 21B are views of an acoustic filter insert for listening to music or protection from impulse noise through the customizable hearing protection devices.

FIG. 22 is an exploded view of the body portion of a customizable hearing protection device with attached eartip and components for assembly and insertion of an acoustic/impulse filter insert.

DETAILED DESCRIPTION

Figure 1A:
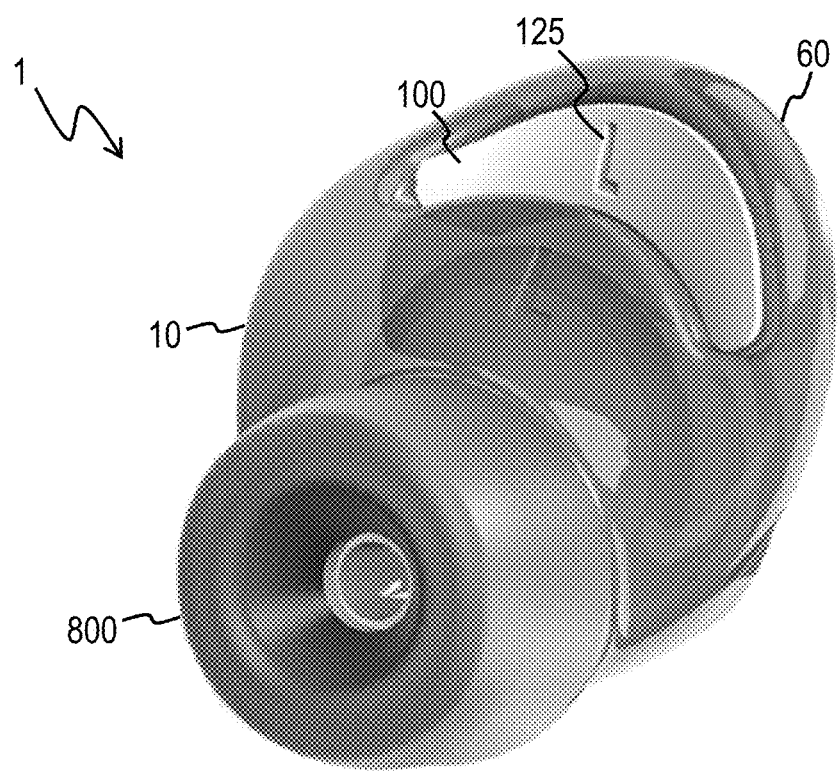
FIG. 1A is a view of a customizable hearing protection device for the left ear of a wearer, including a foam cushion for insertion into the ear and an inserted interchangeable chip.
Figure 1B:
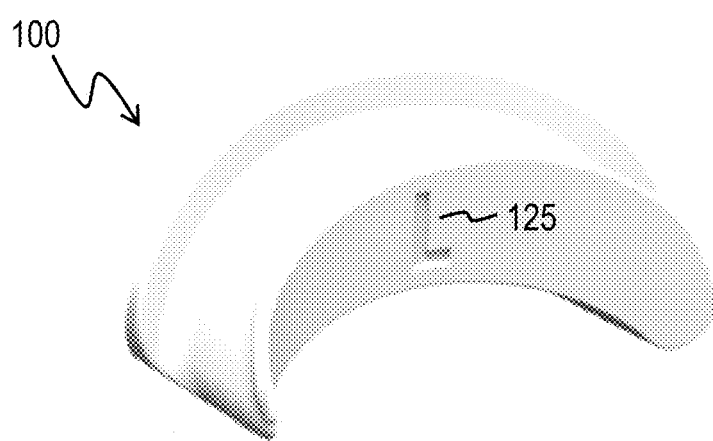
FIG. 1B is a view of an inserted interchangeable chip for the customizable hearing protection device.
Figure 2A:
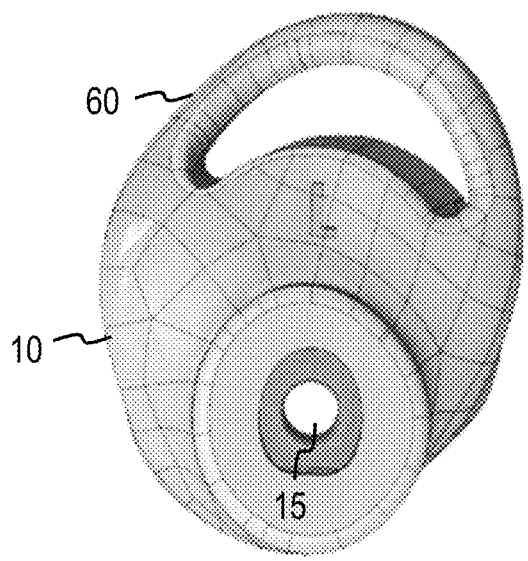
FIG. 2A is a schematic front view of the body portion of a customizable hearing protection device according to embodiments.
Figure 2B:
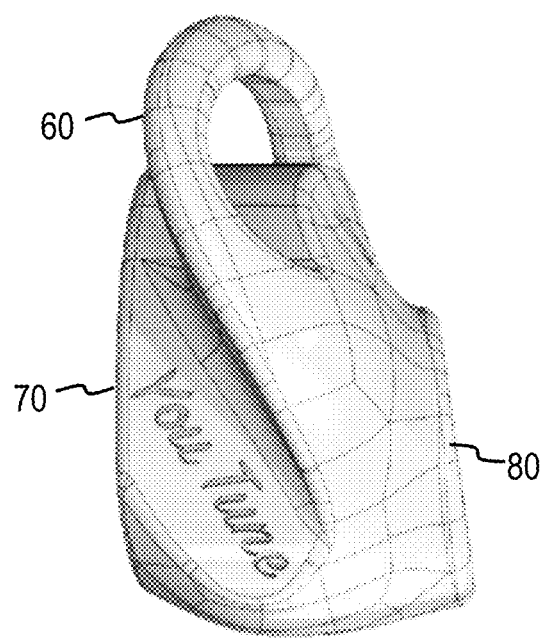
FIG. 2B is a schematic side view of the body portion of a customizable hearing protection device according to embodiments.

Embodiments of this disclosure are directed to customizable hearing protection devices that also are adaptable for use as stereo headphones for listening to audio from an audio source, with or without hearing protection, and quickly interchangeable from configurations providing minimal hearing protection to configurations providing maximum hearing protection, and vice versa. The hearing protection devices are configured for a precise fit into either the left ear or the right ear of a wearer. Referring generally to FIGS. 1A and 2A, which are oriented to show a proximal side 80 of a hearing protection device 1 facing toward the head of a wearer or user, customizable hearing protection devices 1 include a body portion 10. The body portion 10 includes a loop portion 60 that accommodates an interchangeable chip 100 (FIG. 1B). As will be described subsequently in detail, an eartip 800 is attached to the body portion 10 and is suitable for insertion into an ear canal of a wearer of the customizable hearing protection device 1. The interchangeable chip 100 is configured to be insertable into either a left-ear device or a right-ear device and may include markings 125 thereon to indicate into which device the interchangeable chip will fit.

In general, the customizable hearing protection devices according to embodiments of this disclosure are versatile and adaptable to many different applications and end uses, from firing ranges, to race tracks, to battlefields (including communication capabilities with the earphones), to concerts, as a few examples. The interchangeable chip 100 may enhance the versatility of the hearing protection devices and enable customization to the wearer and/or unique advertising possibilities.

Figure 3:
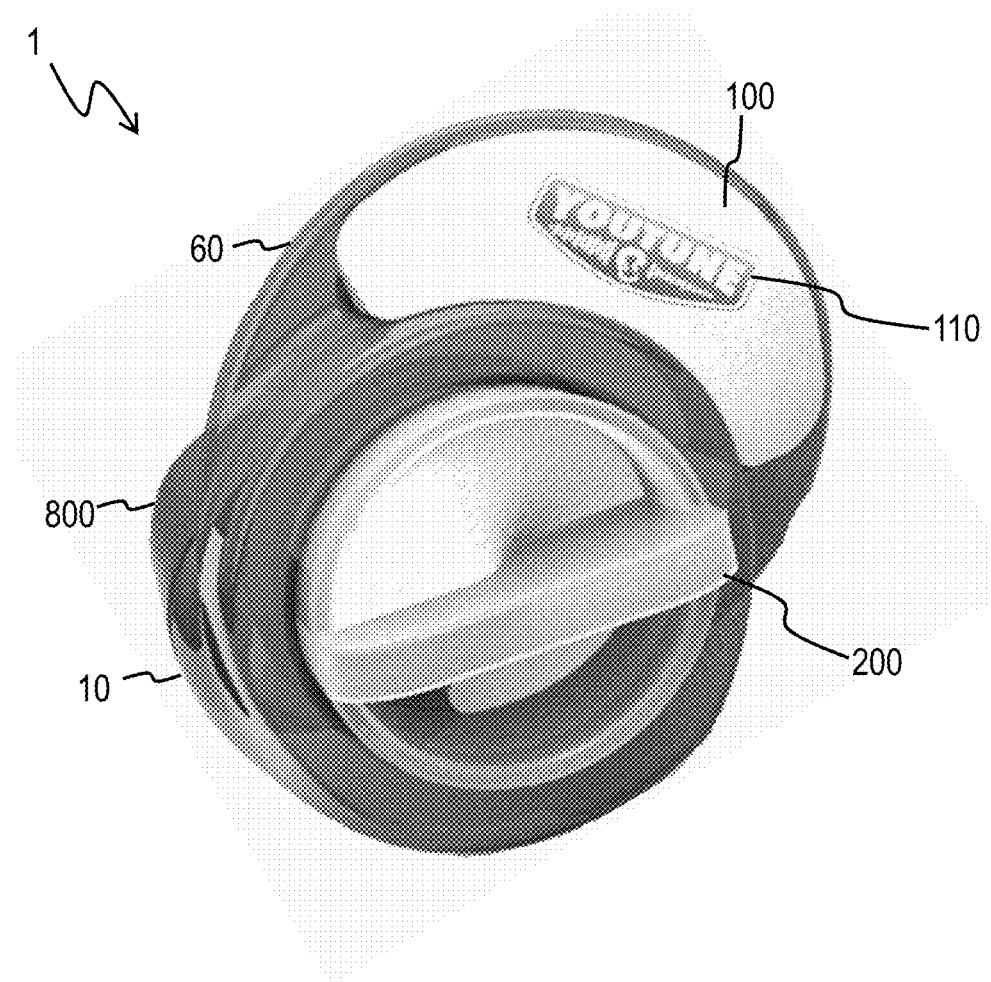
FIG. 3 is a front view of a hearing protection device with an adjustable noise-reduction attachment and interchangeable chip, for which the interchangeable chip includes an example of a customized advertising logo.

Referring to FIG. 3, which shows a distal side of the customizable hearing protection device 1 facing away from the head of the user, the interchangeable chip 100 may include customized indicia 110 on a surface thereof. The customizable hearing protection device 1 also includes a sound modifying insert 200. The sound modifying insert 200 may be any device or apparatus that modifies sound entering into the ear of the wearer from the ambient sound that the wearer would hear without the customizable hearing protection device 1. The sound modifying insert 200 may decrease sound volume, may filter sounds in specific frequency ranges, or may send audio generated by a speaker to the ear of the wearer.

As previously described, the customizable hearing protection devices 1 include a body portion 10. The cross-section of FIG. 4 includes the body portion 10 alone. The cross-section of FIG. 5 includes the body portion 10, the sound modifying insert 200, and the adapter insert 400. Referring jointly to the cross-sections of FIGS. 4 and 5, a channel 20 is defined through the body portion 10 from a distal side 70 of the body portion 10 to a proximal side 80 of the body portion 10 opposite the distal side 70. The sound modifying insert is removably inserted into an outer portion 30 of the channel 20 adjacent to the distal side 70 of the body portion 10 to contact a forward wall 37 of the body portion 10. The outer portion 30 has a first diameter d1. An adapter insert 400, which will be described subsequently, is removably inserted into an inner portion 40 of the channel 20 adjacent to the proximal side 80 of the body portion 10. The inner portion 40 of the channel 20 has a second diameter d2. The second diameter d2 is less than the first diameter d1 of the outer portion 30 of the channel 20. An eartip 800 (FIG. 1A) is mounted to a stem portion 460 of the adapter insert 400 that protrudes from the proximal side 80 of the body portion 10. The channel 20 further includes a middle portion 50 connecting the outer portion 30 and the inner portion 40. The middle portion 50 has a third diameter d3, the third diameter d3 being less than the second diameter d2. The adapter insert 400 has a sound path 420 defined through the adapter insert 400 from an entrance end 430 of the adapter insert 400 to an exit end 440 of the adapter insert 400.

Figure 4:
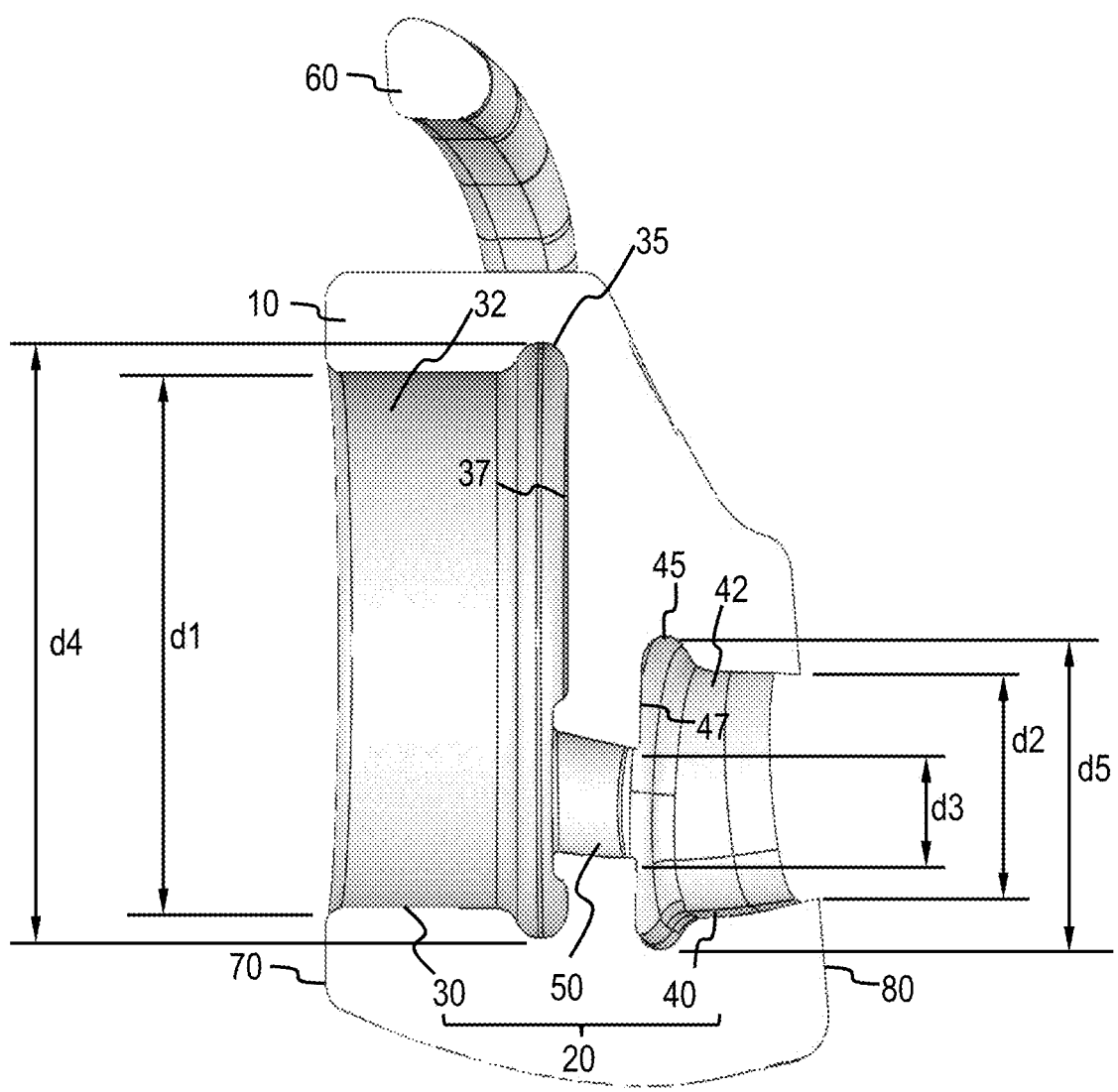
FIG. 4 is a cross-section of a body portion of a customizable hearing protection device.
Figure 5:
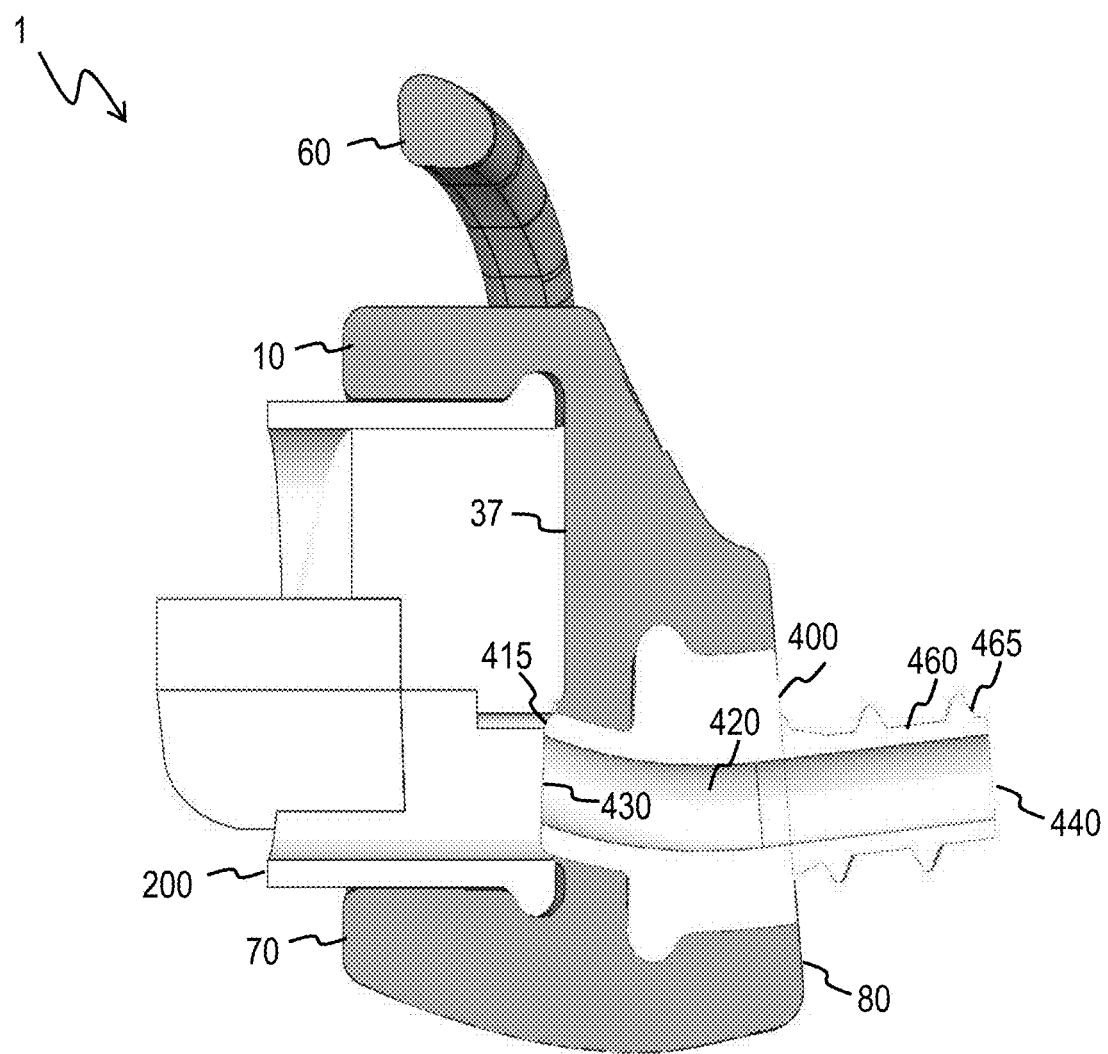
FIG. 5 is a cross-section of a customizable hearing protection device with a noise-reduction filter and adapter insert inserted.
Figure 6A:
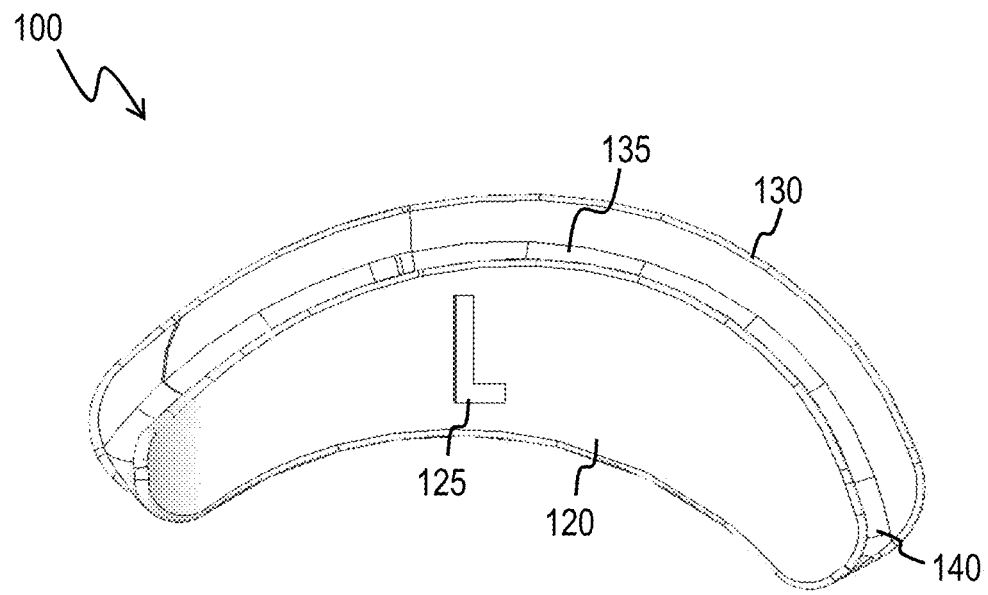
FIG. 6A is a back view of an interchangeable chip for left-ear customizable hearing protection devices.
Figure 6B:
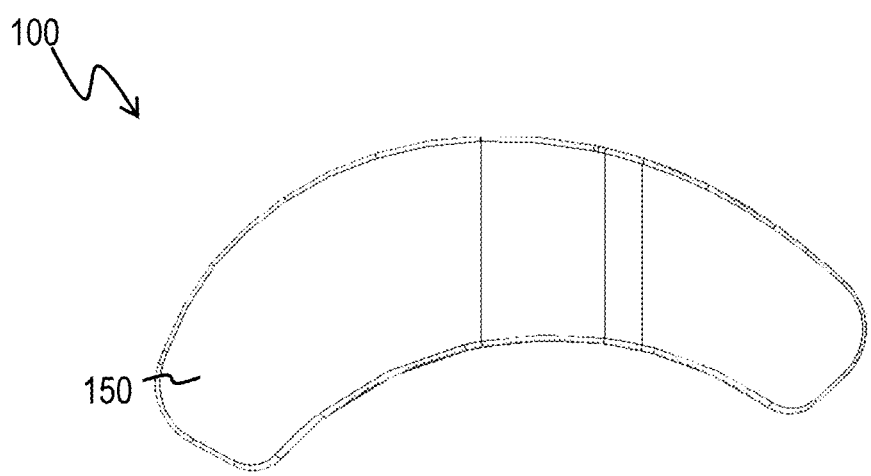
FIG. 6B is a front view of an interchangeable chip for left-ear customizable hearing protection devices.
Figure 6C:
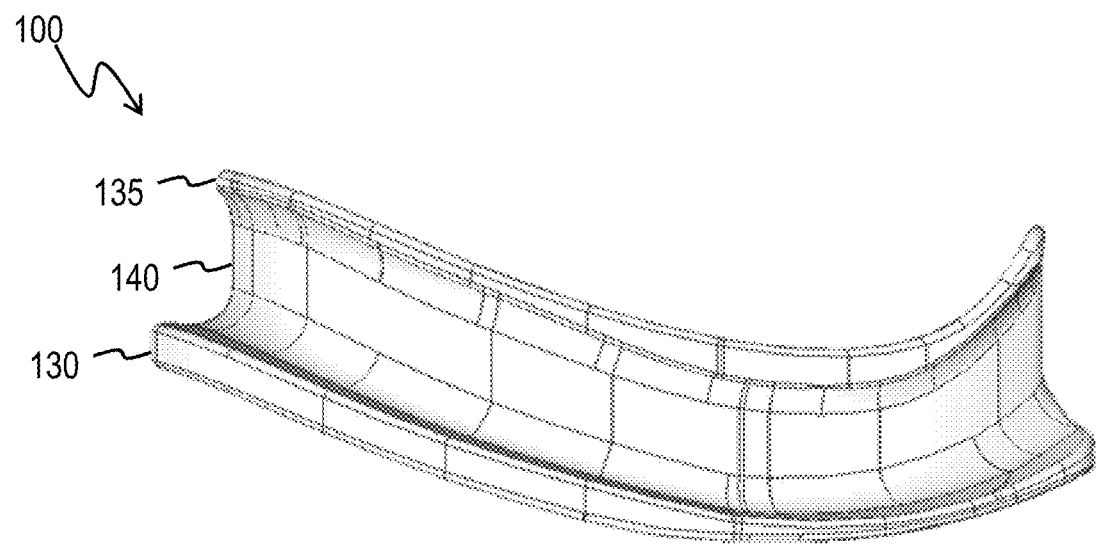
FIG. 6C is a top view of an interchangeable chip for left-ear customizable hearing protection devices.
Figure 6D:
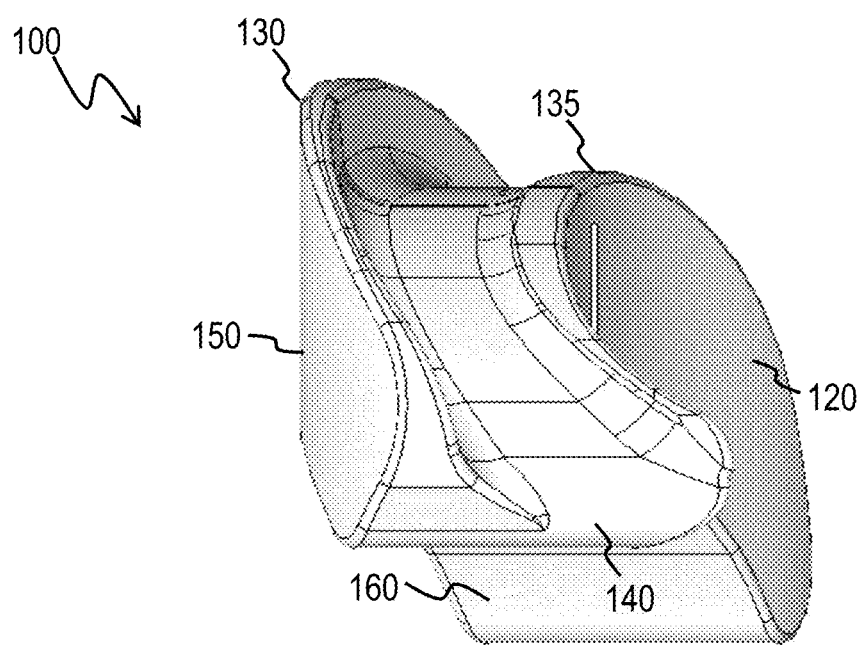
FIG. 6D is a side view of an interchangeable chip for left-ear customizable hearing protection devices.
Figure 7A:
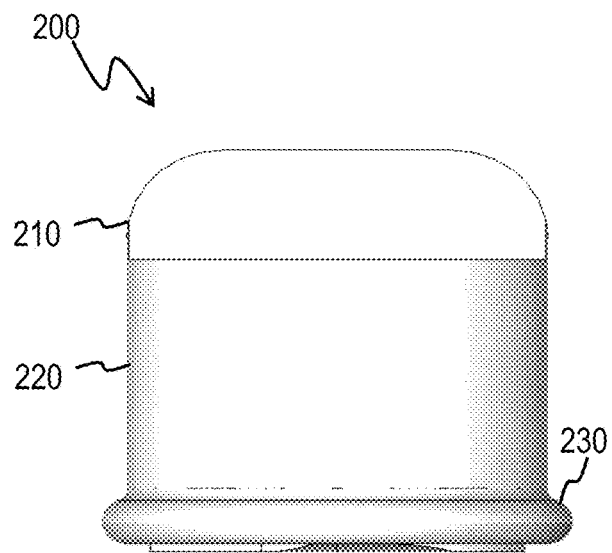
FIGS. 7A-7G are views of a noise-reduction insert as a sound-modifying insert for customizable hearing protection devices according to embodiments.
Figure 7B:
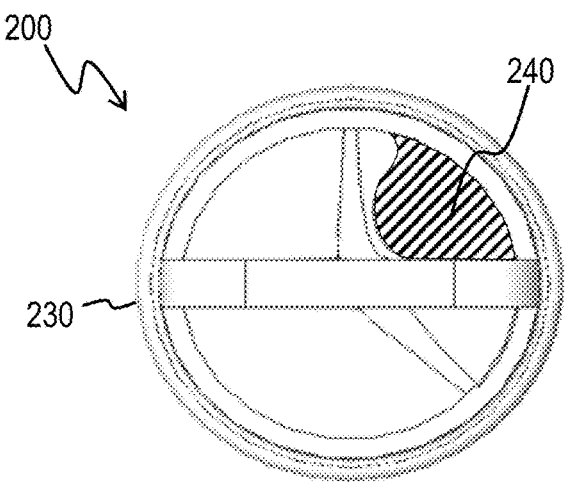
Figure 7C:
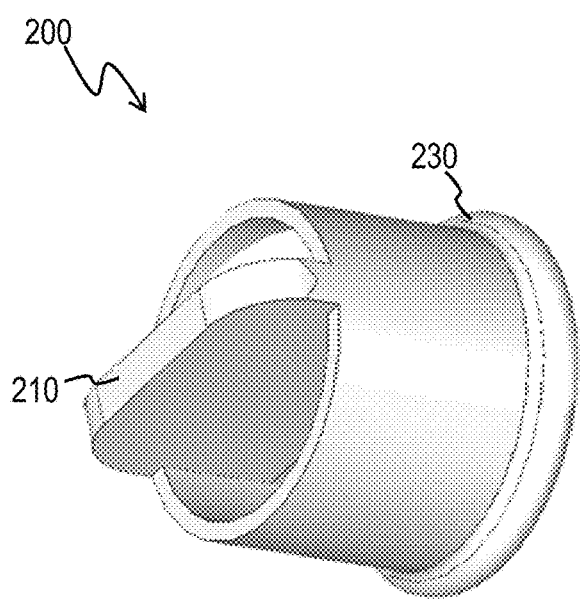
Figure 7D:
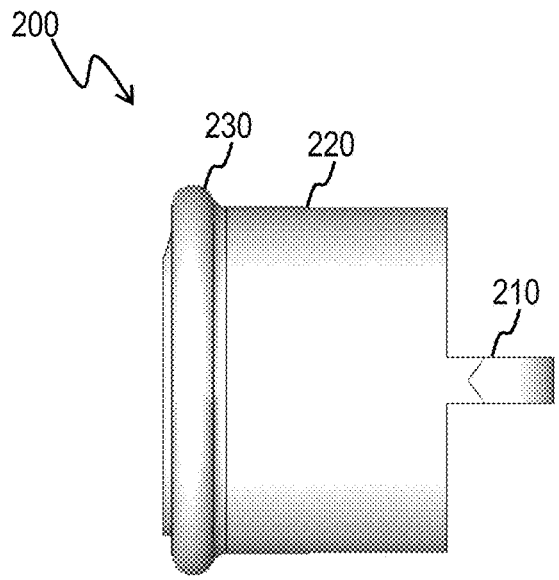
Figure 7E:
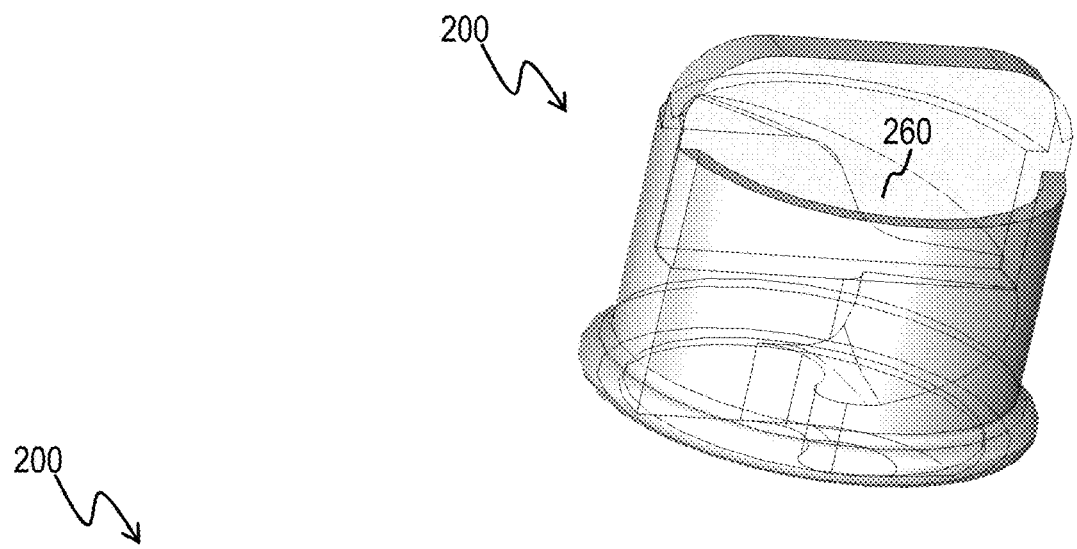
Figure 7F:
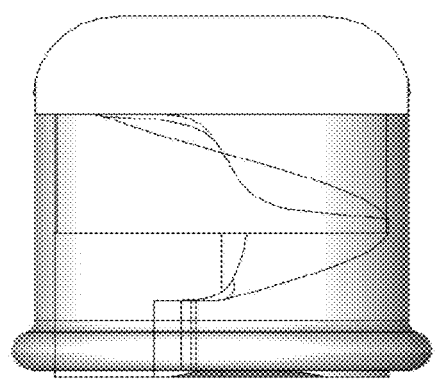
Figure 7G:
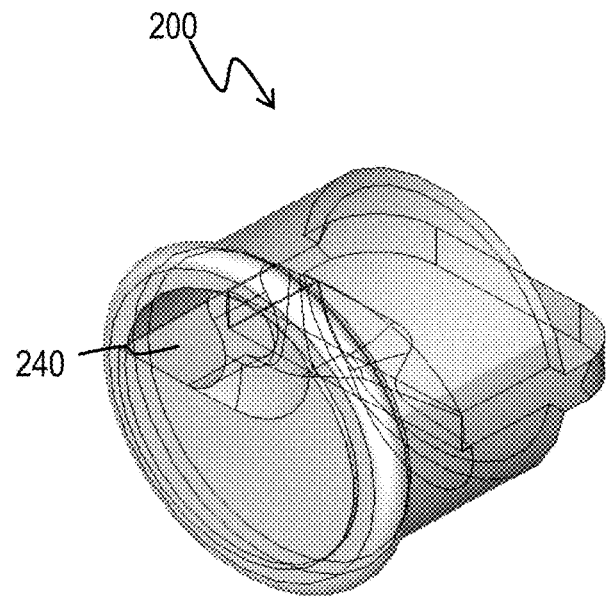

Referring to FIG. 4, the outer portion 30 of the channel 20 may include a main portion 32 with the first diameter d1, and an accessory grasping portion 35 with a fourth diameter d4, the fourth diameter d4 being greater than the first diameter d1. Likewise, the inner portion 40 of the channel 20 may include a main portion 42 with the second diameter d2 and an insert grasping portion 45 with a fifth diameter d5, the fifth diameter d5 being greater than the second diameter d2.

Referring to FIG. 3, in some embodiments, the customizable hearing protection device 1 further includes a loop portion 60 defined in the body portion 10 and an interchangeable chip 100 removably inserted into the loop portion 60. Referring to FIGS. 6A-6D, the interchangeable chip 100 includes a bottom surface 160 that conforms to contours of a surface of the body portion 10 and a top groove 140 defined between a front edge 130 and a rear edge 135. The front edge 130 is also a top edge of an outer surface 150 of the interchangeable chip 100. The rear edge 135 is also a top edge of an inner surface 120 of the interchangeable chip 100. When the interchangeable chip 100 is inserted into the body portion 10, the top groove 140 engages the loop portion 60 of the body portion 10. The outer surface 150 of the interchangeable chip 100 may include customized indicia 110 (FIG. 3). The customized indicia 110 may be applied by any available method for applying indicia to a plastic surface. In some embodiments, the customized indicia 110 may be applied by in-mold labeling. The interchangeable chip 100 locks into place using a friction fit. The shape of the interchangeable chip 100 may follow the shape of the concha area in the average human ear. The inclusion of the interchangeable chip 100 may also increase earplug retention in the concha region of the human ear.

Figure 20:
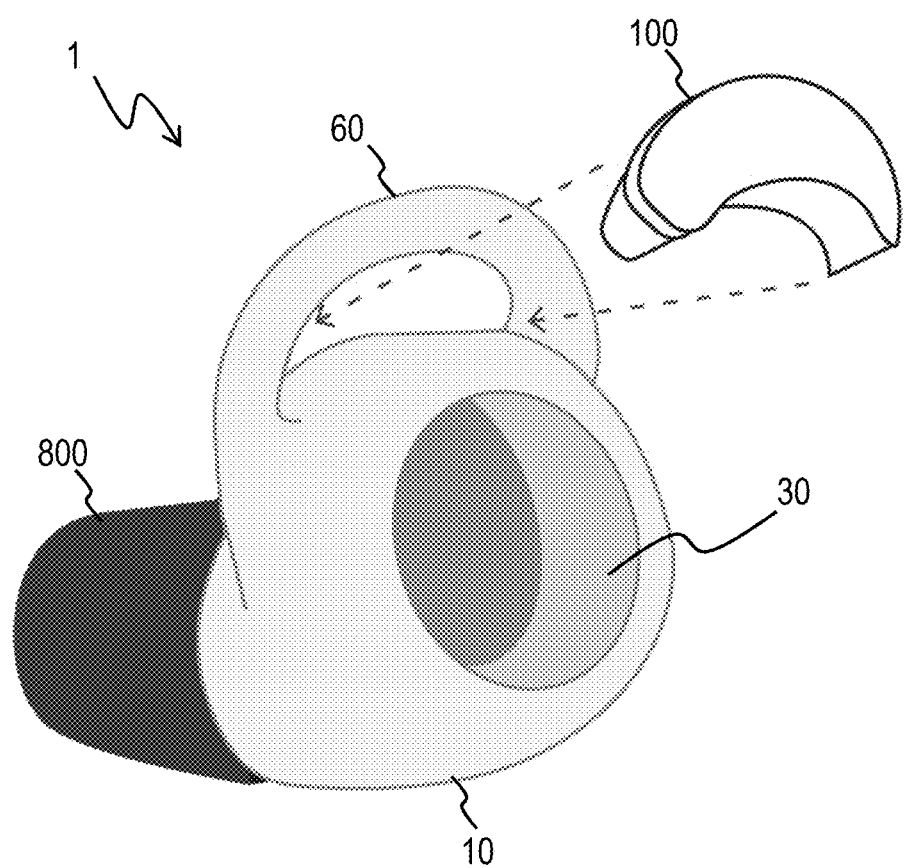
FIG. 20 is a schematic showing insertion of an interchangeable chip into the body portion of a customizable hearing protection device.

The interchangeable chip 100 may include customized indicia 110 such as text or logos. The interchangeable chip 100 may include corporate branding, university marching band logos, NASCAR/formula driver numbers, for example. The interchangeable chip 100 may also be adapted for alerting purposes and may include a battery and a light source such as a light-emitting diode (LED) to illuminate the body portion 10. The friction fit of the interchangeable chip 100 may be accomplished by the contours of the loop portion 60 of the hearing protection device in combination with the shape of the interchangeable chip 100. In some embodiments, the shapes of interchangeable chips 100 for left-ear and right-ear devices are mirror images of each other. FIG. 20 is a schematic illustrating insertion of the interchangeable chip 100 into the body portion 10, when the body portion 10 has an eartip 800 attached.

Figure 24A:
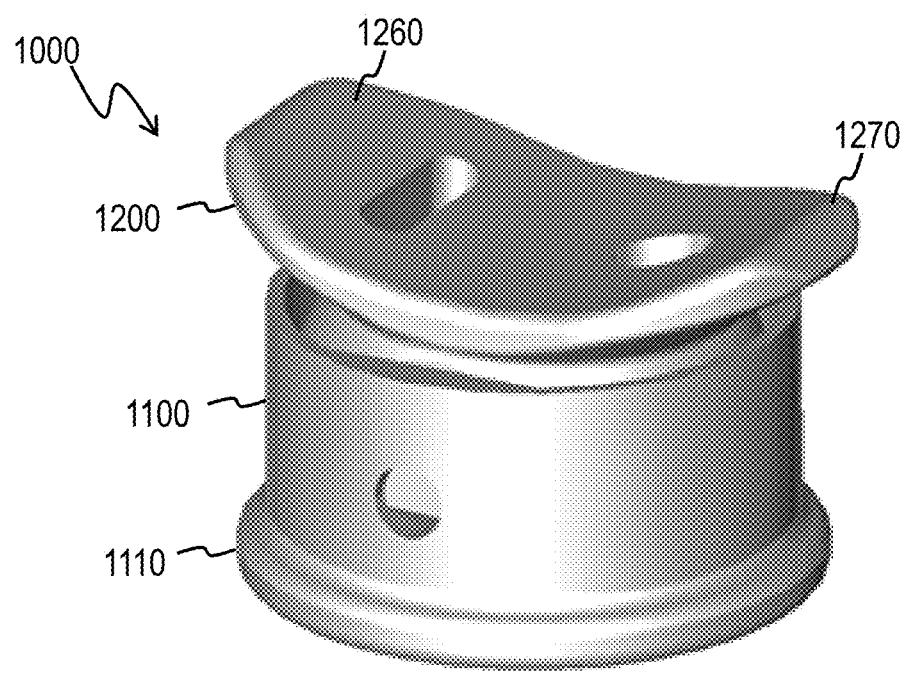
FIG. 24A is a top elevation of a sound modifying insert according to embodiments, in which the sound modifying insert is a rocker switch.
Figure 24B:
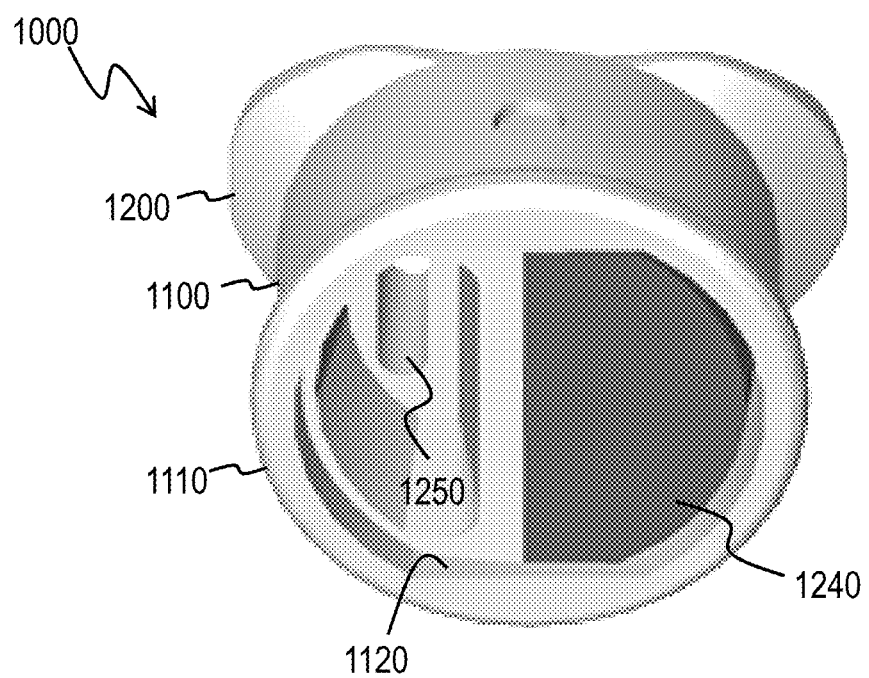
FIG. 24B is a bottom elevation of the rocker switch of FIG. 24A.

As previously described, the customizable hearing protection device 1 includes a sound modifying insert. In various embodiments, the sound modifying insert may be selected from an adjustable noise-reduction attachment 200 (FIGS. 7A-7G), a stepped noise-reduction attachment (FIGS. 9A and 9B), a speaker 900 (FIGS. 19A and 19B), a high-fidelity music/impulse cartridge insert 950 (FIGS. 21A, 21B, and 22), or a rocker switch (FIGS. 24A and 24B).

Referring to FIGS. 7A-7G, in some embodiments of the customizable hearing protection device 1, the sound modifying insert is an adjustable noise-reduction attachment 200. The adjustable noise-reduction attachment 200 includes a rotatable body 220 that is rotatable within the outer portion 30 of the channel 20. The rotatable body 220 may include a handle portion 210 that a wearer may use to rotate the rotatable body 220. The rotatable body 220 may include a retaining edge 230 that fits into the accessory grasping portion 35 of the outer portion 30 of the channel 20 of the body portion 10.

Figure 8:
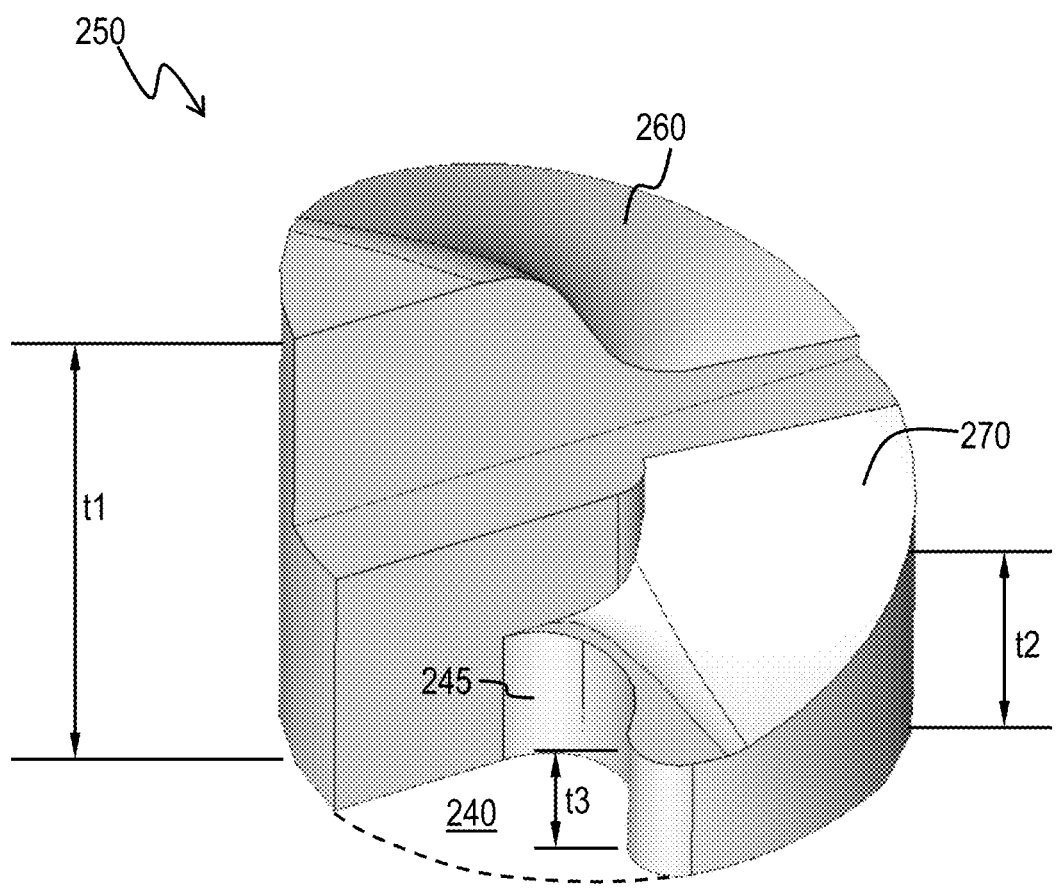
FIG. 8 is a side elevation of an inner portion of a noise-reduction insert for customizable hearing protection devices according to embodiments.
Figure 18A:
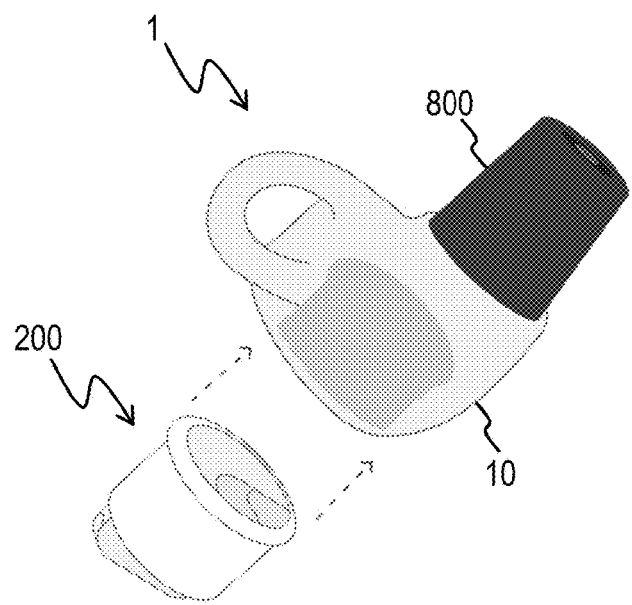
FIGS. 18A and 18B are schematics showing insertion of an adjustable noise-reduction attachment into the body portion of a customizable hearing protection device.
Figure 18B:
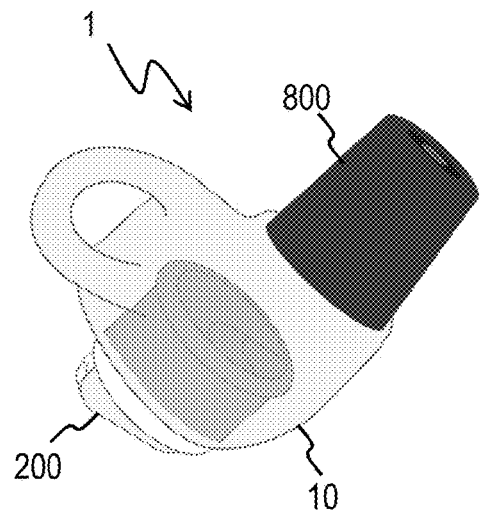

Referring to FIG. 8, the rotatable body 220 has a solid center portion 250 with a thickness t1, t2, t3, that varies with respect to an angle of rotation of the rotatable body 220, whereby rotation of the rotatable body 220 causes a variable thickness of the solid center portion 250 to block entrance of sound into the sound path 420 of the adapter insert 400. The variable thickness may be accomplished by a spiral-type configuration of the solid center portion 250 including, for example, a thick spiral portion 260 and a thin spiral portion 270. The solid center portion may also include minimal-attenuation groove 245 that defines a minimal-attenuation zone 240, in which no sound-blocking material blocks entrance of sound into the channel 20 of the body portion 10 when the rotatable body 220 is rotated over the minimal-attenuation zone 240. The adjustable noise-reduction attachment 200 may operate in a manner similar to the attachment described in commonly-owned U.S. Pat. No. 8,931,489, incorporated herein by reference in its entirety. The interaction between the retaining edge 230 and the accessory grasping portion 35 not only retains the rotatable body 220 within the body portion 10 but also enables increased pressure of the rotatable body 220 against the adapter insert 400 for a greater level of noise reduction. FIGS. 18A and 18B are schematics illustrating insertion of the adjustable noise-reduction attachment 200 into the body portion 10, when the body portion 10 has an eartip 800 attached.

Figure 9A:
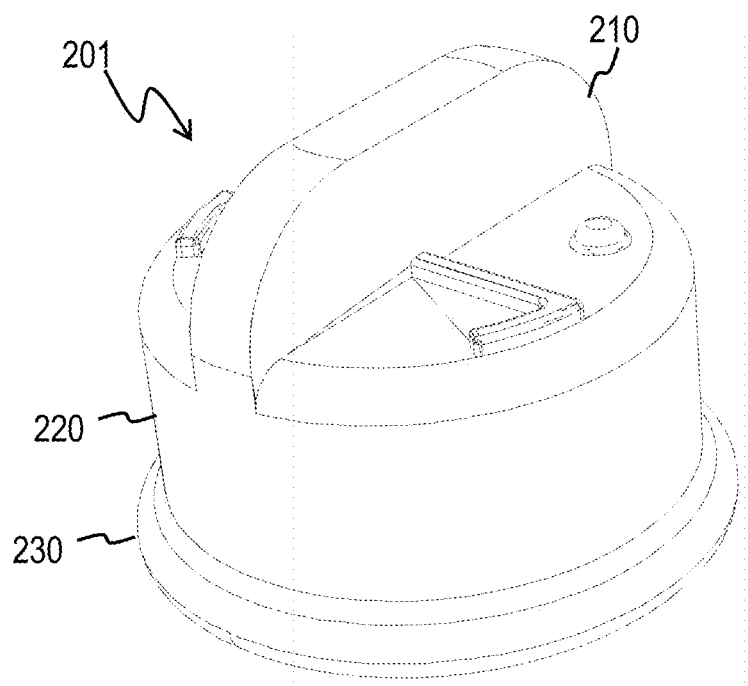
FIG. 9A is a side elevation of a stepped noise-reduction insert as a sound-modifying insert for customizable hearing protection devices according to embodiments.
Figure 9B:
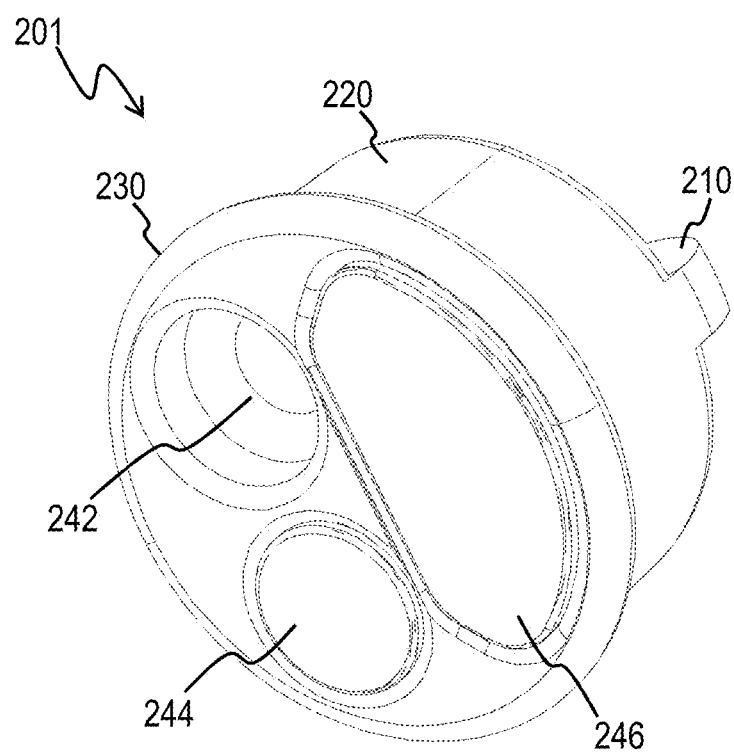
FIG. 9B is a bottom elevation of a stepped noise-reduction insert as a sound-modifying insert for customizable hearing protection devices according to embodiments.

Referring to FIGS. 9A and 9B, in further embodiments, the sound modifying insert may be a stepped adjustable noise-reduction attachment 201. Similar to the adjustable noise-reduction attachment 200 previously described, stepped adjustable noise-reduction attachment 201 includes a rotatable body 220 that is rotatable within the outer portion 30 of the channel 20. The rotatable body 220 includes a handle portion 210 that a wearer may use to rotate the rotatable body 220. The rotatable body 220 of the stepped adjustable noise-reduction attachment 201 includes a retaining edge 230 that fits into the accessory grasping portion 35 of the outer portion 30 of the channel 20 of the body portion 10. The rotatable body 220 has a center portion that includes a minimal attenuation zone 242, a moderate attenuation zone 244, and a maximum attenuation zone 246. In embodiments, the minimal attenuation zone 242 may be a hole into the body of the stepped adjustable noise-reduction attachment 201, such that the minimal attenuation zone 242 functions essentially as an extension cavity of the middle portion 50 of the body portion 10. The moderate attenuation zone 244 and the maximum attenuation zone 246 may be formed as pads or sound-reducing structures with varying amounts or thicknesses of a blocking material, such as a noise-reducing foam, or a thermoplastic elastomer such as Santoprene®. For example, the moderate attenuation zone 244 may be formed of a padding of one thickness, while the maximum attenuation zone 246 is formed of a padding of a thickness greater than that of the moderate attenuation zone 244. By the configuration of the minimal attenuation zone 242, the moderate attenuation zone 244, and the maximum attenuation zone 246, an amount of material reducing or blocking an amount of sound that enters the middle portion 50 of the channel 20 varies with respect to an angle of rotation of the rotatable body 220 of the stepped adjustable noise-reduction attachment 201.

In the example embodiment of FIGS. 9A and 9B, when the minimal attenuation zone 242 aligns with the middle portion 50 of the channel 20 in the body portion 10, sound volume entering the customizable hearing protection device 1 may be reduced by a minimal amount of 0 dB to 6 dB. When the moderate attenuation zone 244 aligns with the middle portion 50 of the channel 20 in the body portion 10, sound volume entering the customizable hearing protection device 1 may be reduced by a greater amount of 18 dB to 23 dB. When the maximum attenuation zone 246 aligns with the middle portion 50 of the channel 20 in the body portion 10, sound volume entering the customizable hearing protection device 1 may be reduced by a maximum amount of up to 26 dB. The interaction between the retaining edge 230 and the accessory grasping portion 35 not only retains the rotatable body 220 within the body portion 10 but also enables increased pressure of the rotatable body 220 against the adapter insert 400 for a greater level of noise reduction.

Figure 19A:
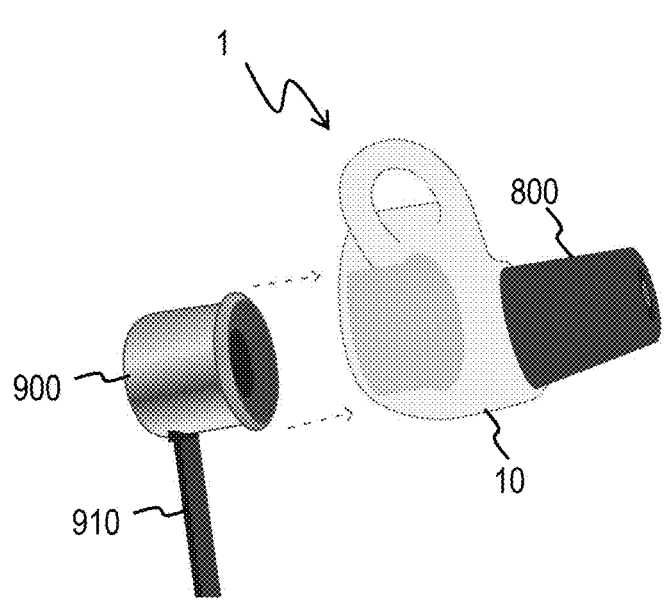
FIGS. 19A and 19B are schematics showing insertion of a speaker as a sound-modifying insert into the body portion of a customizable hearing protection device.
Figure 19B:
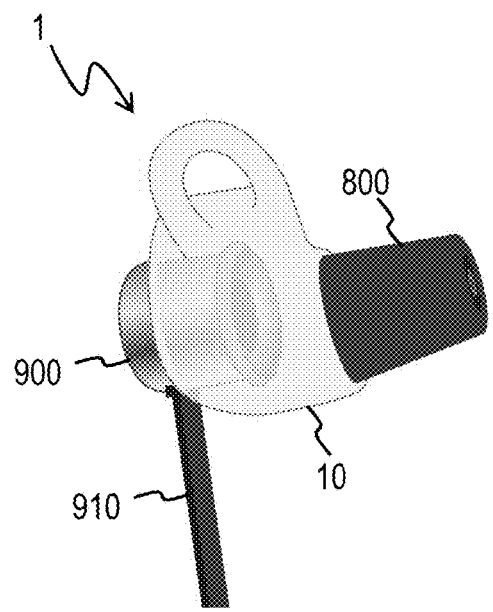

Referring to FIGS. 19A and 19B, in some embodiments of the customizable hearing protection device 1, the sound modifying device may be a speaker 900. The speaker 900 may have a speaker wire 910 connected to a power source (not shown) or a signal source (not shown). Alternatively, the speaker 900 may be wirelessly driven by signals from a broadcasting source (not shown). FIGS. 19A and 19B are schematics illustrating insertion of the speaker 900 into the body portion 10, when the body portion 10 has an eartip 800 attached.

Referring to FIGS. 21A, 21B, and 22, in some embodiments of the customizable hearing protection device 1, the sound modifying device may be an acoustic noise filter 950. The acoustic noise filter 950 is configured to provide a tuned, flat attenuation response over the entire frequency range. Flat attenuation allows users to enjoy the natural sound of live music, but at a safer lower level, without a more severe reduction of high-frequency sounds compared to low-frequency sounds. Such acoustic noise filters are designed for listening to music, because high-frequency sounds are not overly attenuated so as to distort the sound of the music. Impulse filters reduce peak sound pressure produced by gunshots or explosions. Hearing is protected while still being able to communicate and hear surrounding sounds. Minimal sound reduction is provided for quiet sound of interest and noise protection to hazardous impulse sounds. Various views of an acoustic noise filter for use with the hearing protection devices according to embodiments are provided in FIGS. 21A and 21B. The acoustic noise filter 950 may include a filter frame 960 having a retention ridge 965 to retain the acoustic noise filter 950 in the body portion. As shown in the exploded view of FIG. 22, the acoustic noise filter 950 may be an assembly of components that are together inserted into the body portion 10. The assembly of multiple components may include the filter frame 960 and a filter device 970 removably insertable into the filter frame. Cuts on the top surface of the filter device 970 are configured to enable passage of sound waves into the filter device 970 in an optimal manner. The sound waves then pass through the filter device 970 and the filter frame 960 to emerge through the sound exit hole 980 into the middle portion 50 of the body portion 10 of the customizable hearing protection device 1. In embodiments for which the adapter insert includes a protuberance, the protuberance may extend partly into the sound exit hole 980 of the filter frame 960. Also the width and height of the acoustic noise filter 950 are configured to provide proper attenuation of sound.

Figure 23:
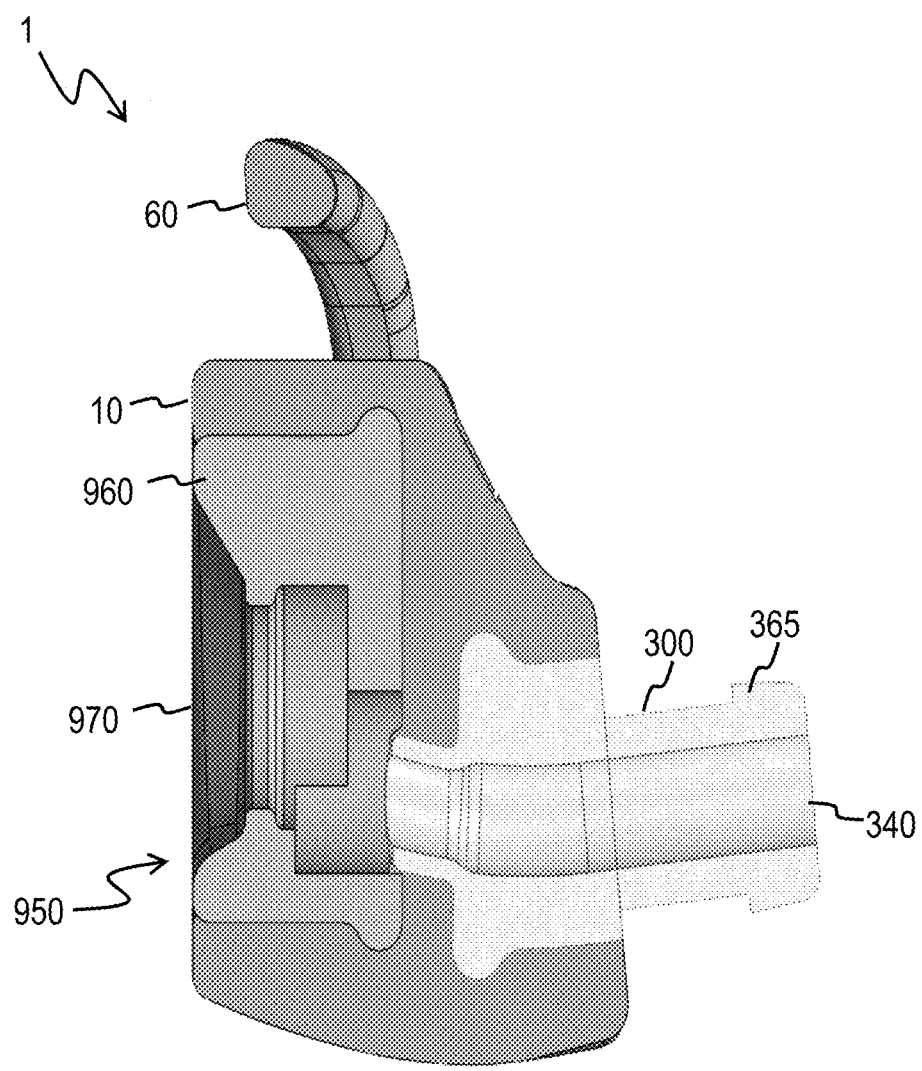
FIG. 23 is a cross-section of a customizable hearing protection device with inserted interchangeable high-fidelity music/impulse cartridge insert and inserted interchangeable high-fidelity music/impulse adapter insert including a noise-reduction protuberance.

As an example embodiment, FIG. 23 is a cross-section of a customizable hearing protection device 1 with a removably inserted acoustic noise filter 950 and a removably inserted unthreaded high-fidelity adapter insert 300.

Figure 25A:
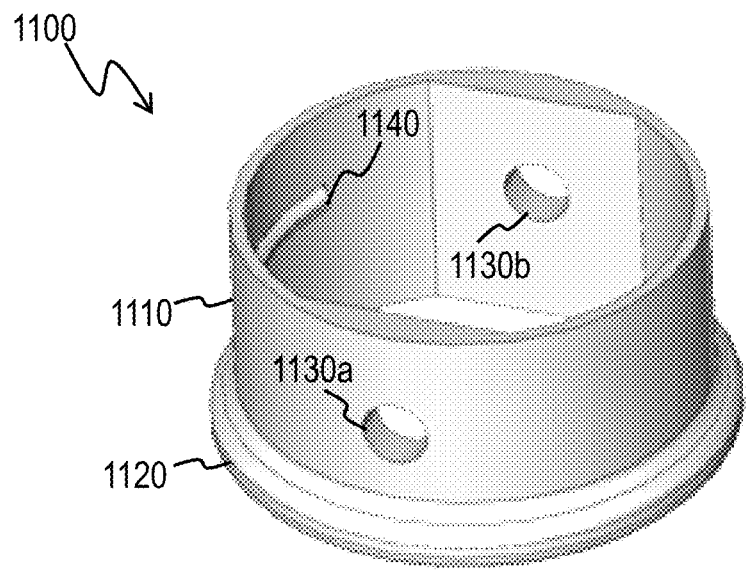
FIG. 25A is a top elevation of an outer case of the rocker switch of FIG. 24A.
Figure 25B:
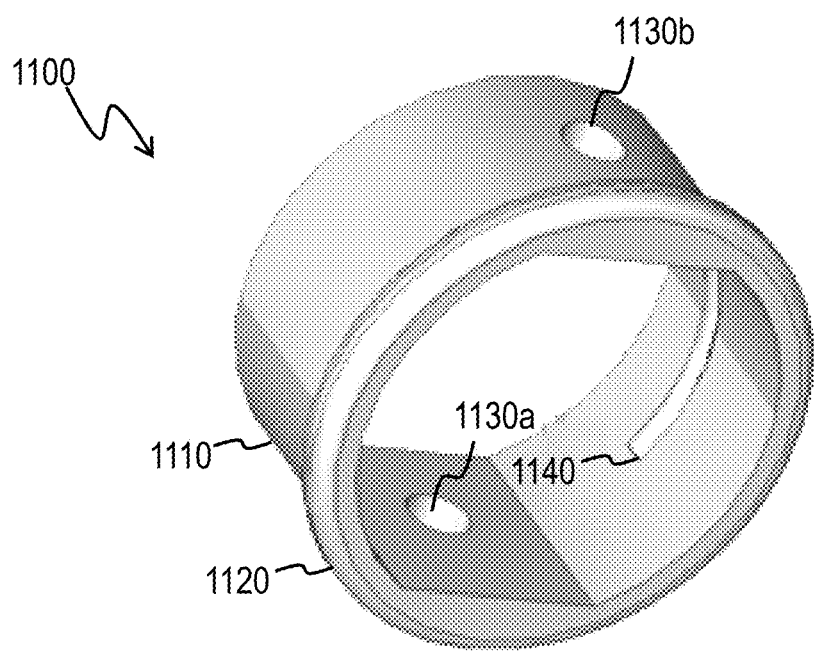
FIG. 25B is a bottom elevation of an outer case of the rocker switch of FIG. 24A.

Referring to FIGS. 24A and 24B, in some embodiments of the customizable hearing protection device 1, the sound modifying device may be a rocker switch 1000. The rocker switch 1000 may be an assembly composed of a switch shell 1100 (FIGS. 25A and 25B) and a rocking component 1200 (FIGS. 26A-26C) tiltably mounted inside of the switch shell 1100. The switch shell 1100 includes a retention ridge 1110 to retain the rocker switch 1000 by friction fit in the outer portion 30 of the channel 20 of the body portion 10. The switch shell 1100 further includes swivel holes 1130*a*, 1130*b*, into which the rocking component 1200 is mounted. The switch shell 1100 further includes inner ribs 1140 to lock the rocking component 1200 into either the open state or the closed state, as will be described subsequently.

Figure 26A:
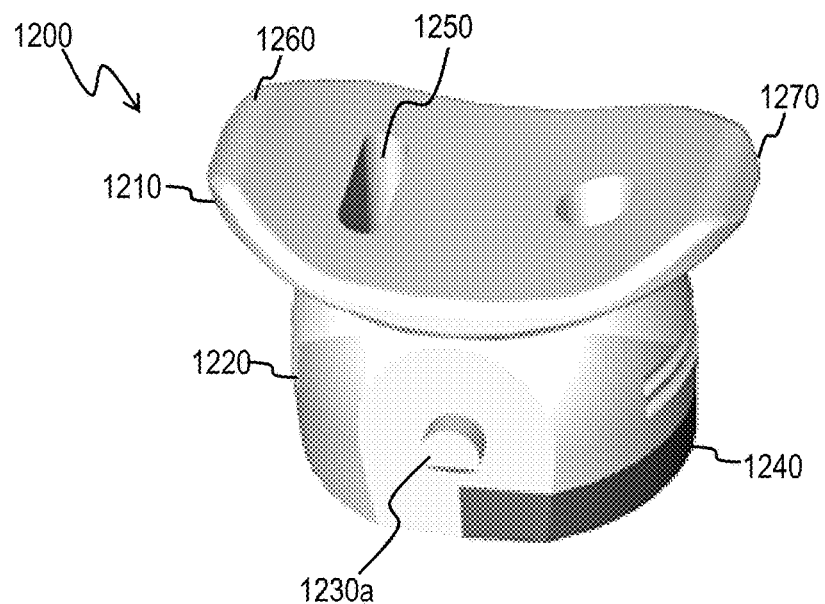
FIG. 26A is a top elevation of an outer case of the rocker switch of FIG. 24A.
Figure 26B:
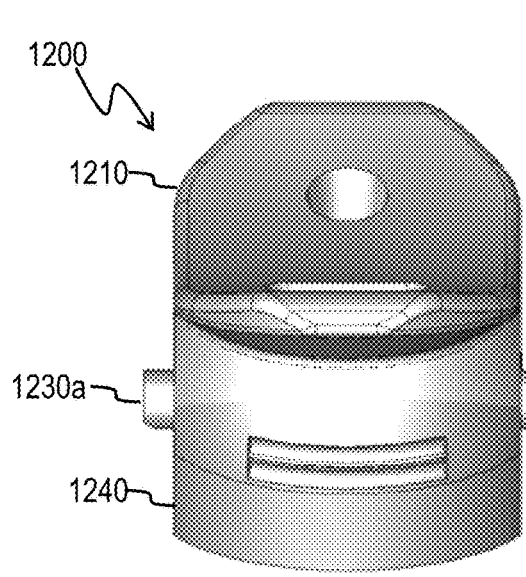
FIG. 26B is a side elevation of an outer case of the rocker switch of FIG. 24A.
Figure 26C:
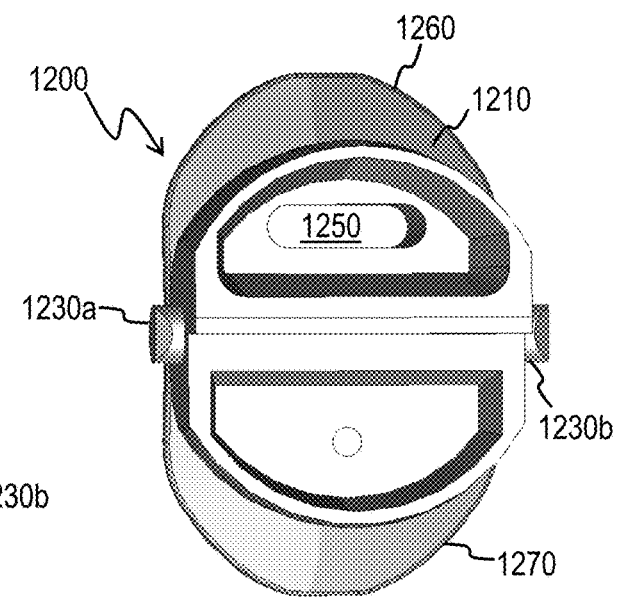
FIG. 26C is a bottom elevation of an outer case of the rocker switch of FIG. 24A.

Referring to FIGS. 26A-26C, the rocking component 1200 of the rocker switch 1000 includes a rocker body 1220 and a press plate 1210 on one end of the rocker body 1220. The press plate 1210 has an opening end 1260 and a closing end 1270. The press plate 1210 further has a sound hole 1250 defined therein. The rocking component 1200 further includes two side pins 1230*a*, 1230*b* that engage into respective swivel holes 1130, 1130*b* of the switch shell 1100. The side pins 1230*a*, 1230*b* have a size appropriate to provide mechanical stability to the rocking component 1200 while also permitting the rocking component 1200 to swivel on an axis through the centers of the side pins 1230*a*, 1230*b*. The rocking component 1200 further includes a muffling pad 1240 on a side opposite the press plate 1210.

Referring back to FIGS. 24A and 24B in view of FIG. 4, the rocking component 1200 is seated inside the switch shell 1100 so that a rim space 1120 remains open underneath or behind the rocking component 1200, directly inside the retention ridge 1110. When the rocker switch 1000 is inserted into the outer portion 30 of the channel 20 of the body portion 10 of the customizable hearing protection device 1, the muffling pad 1240 is oriented to face the middle portion 50 of the channel 20. During use of the rocker switch 1000, the middle portion 50 either may be empty or may be filled with a protuberance from an adapter insert.

Upon insertion into the body portion 10, the rocker switch 1000 has two possible states: an open state, in which sound passes through the customizable hearing protection device 1 unattenuated, and a closed state, in which maximum sound attenuation or volume decrease is activated for the customizable hearing protection device 1. The user may toggle the rocker switch 1000 at will from the open state to the closed state, by pressing the opening end 1260 toward the switch shell 1100, or from the closed state to the open state by pressing the closing end 1270 toward the switch shell 1100. While the rocker switch 1000 is in the open state, sound waves from the ambient environment enter through the sound hole 1250 and pass through the rocker switch 1000 until reaching the rim space 1120. Upon reaching the rim space 1120, the sound waves are deflected downward and into the middle portion 50 of the channel 20, whereupon the sound waves may continue through the adapter insert in the inner portion 40 of the channel and finally into the ear of the wearer. While the rocker switch 1000 is in the closed state, sound waves from the ambient environment still enter through the sound hole 1250 and pass through the rocker switch 1000 until reaching the rim space 1120. However, in the closed state of the rocker switch 1000, the muffling pad is firmly pressed over the opening to the middle portion 50 of the channel, thereby preventing the sound waves from reaching the ear of the wearer to the maximum extent possible for the customizable hearing protection device 1. Thereby, the wearer can easily and quickly change the customizable hearing protection device 1 to have essentially normal hearing in the open state to having maximum hearing protection in the closed state.

As previously described, the customizable hearing protection device 1 further includes an adapter insert removably inserted into an inner portion of the channel adjacent to the proximal side of the body portion. The adapter insert may be chosen by the wearer of the customizable hearing protection device 1 based on the wearer's desired use at a given time. The adapter insert itself is interchangeable. In various embodiments, the adapter insert may be chosen from an unthreaded high-fidelity adapter insert 300 (FIGS. 10A, 10B, and 10C), a threaded noise reduction adapter insert 400 (FIGS. 11A and 11B), a threaded adapter insert 600 (FIGS. 12A and 12B), or an unthreaded music adapter insert 700 (FIGS. 13A and 13B). The various types of adapter inserts will now be described in detail.

Figure 10A:
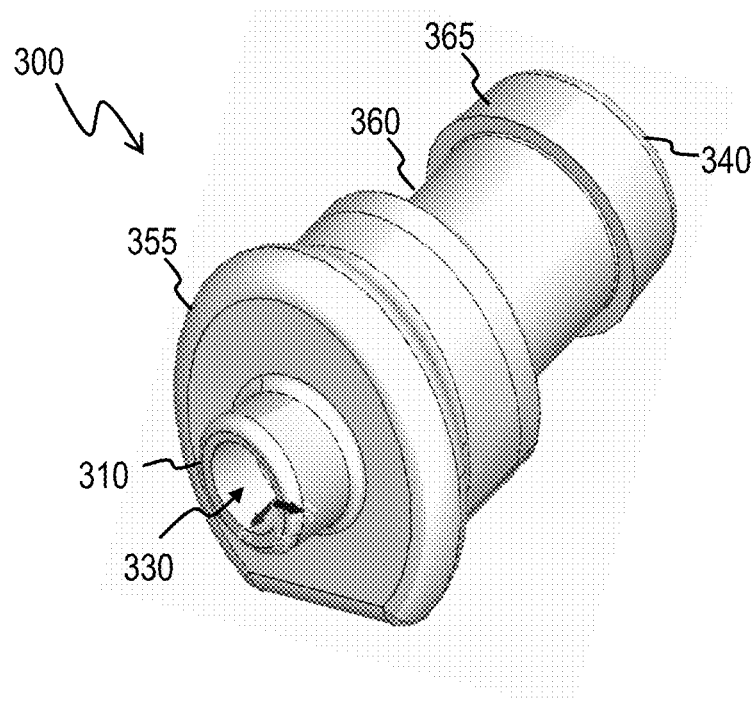
FIG. 10A is a view of an unthreaded high-fidelity adapter insert for a customizable hearing protection device.
Figure 10B:
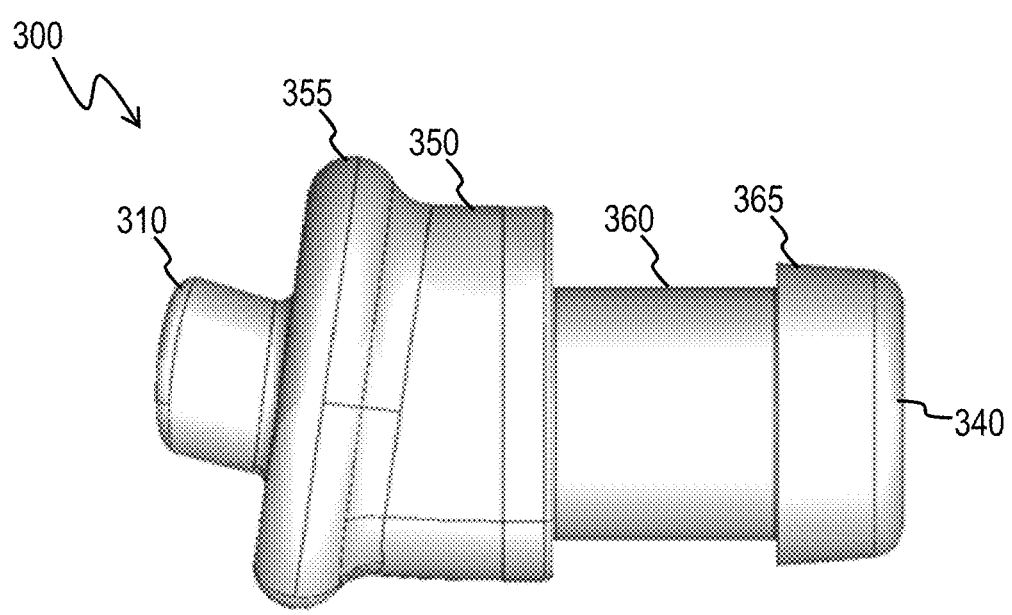
FIG. 10B is a side view of the unthreaded high-fidelity adapter insert of FIG. 10A.
Figure 10C:
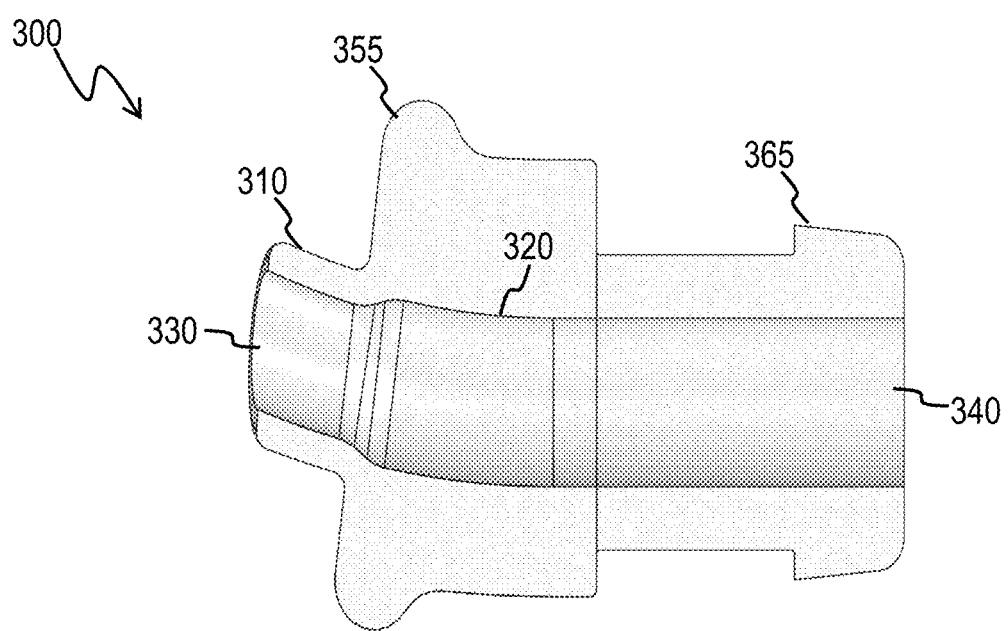
FIG. 10C is a cross-section of the unthreaded high-fidelity adapter insert of FIGS. 10A and 10B.

Referring to FIGS. 10A and 10B, the unthreaded high-fidelity adapter insert 300 is an adapter insert especially well suited both for listening to music in combination with a high-fidelity music cartridge insert described herein while preserving enjoyment of a wide dynamic frequency range and also for providing protection against impulse sounds when used in combination with various noise-reduction inserts described herein. The unthreaded high-fidelity adapter insert 300 includes a neck portion 350, a retention ridge 355, a stem portion 360, a tip grasping portion 365, and a protuberance 310. A sound path is defined inside the unthreaded high-fidelity adapter insert 300 from an entrance end 330 of the unthreaded high-fidelity adapter insert 300 to an exit end 340 of the unthreaded high-fidelity adapter insert 300. The retention ridge 355 is configured to engage the insert grasping portion 45 of the inner portion 40 of the channel 20 of the body portion 10, thereby preventing dislodging of the unthreaded high-fidelity adapter insert 300 while the customizable hearing protection device 1 is inserted into the ear. The tip grasping portion 365 is configured to stably hold an eartip. The sound path includes a curvature, by which the sound path is not strictly horizontal but begins in a slightly downward orientation and bends to an essentially horizontal orientation. When the unthreaded high-fidelity adapter insert 300 is in the body portion 10 of the customizable hearing protection device 1, the protuberance 310 is disposed within the middle portion 50 of the channel 20 of the body portion 10. The protuberance 310 is configured to enter into the sound modifying insert 200 (FIGS. 7A-7G), 201 (FIGS. 9A and 9B), 950 (FIG. 21A), such that pressure of the sound modifying insert surrounding the protuberance 310 provides a greater seal and, thereby, a greater amount of noise reduction.

Figure 11A:
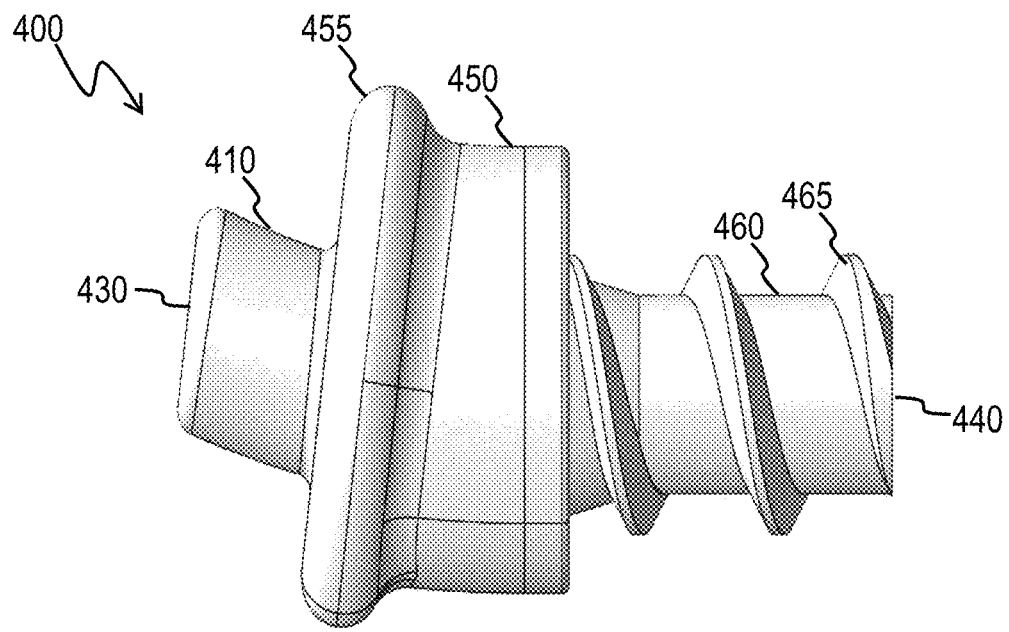
FIG. 11A is a side view of an interchangeable threaded noise reduction adapter insert for attaching to the customizable hearing protection device.
Figure 11B:
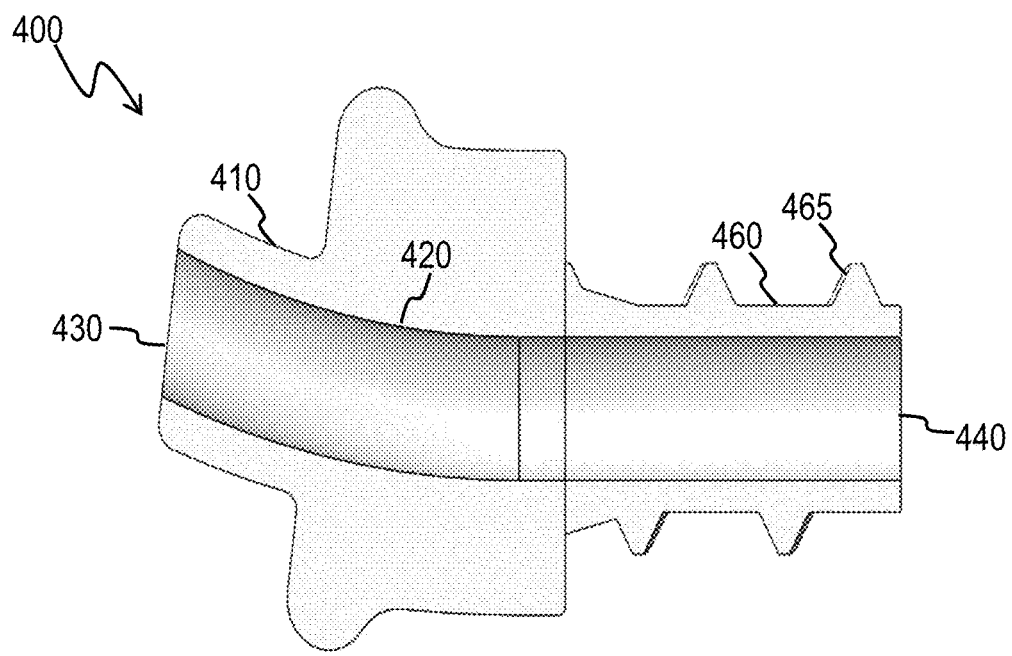
FIG. 11B is a cross-section of the interchangeable threaded noise reduction adapter insert of FIG. 11A.
Figure 15A:
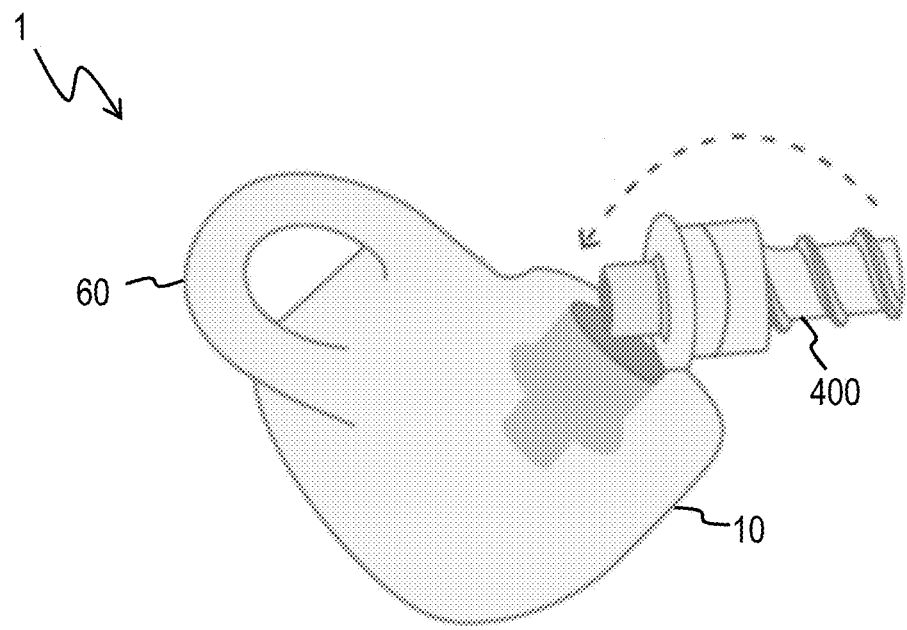
FIGS. 15A and 15B are schematics showing insertion of an adapter insert into the body portion of a customizable hearing protection device.
Figure 15B:
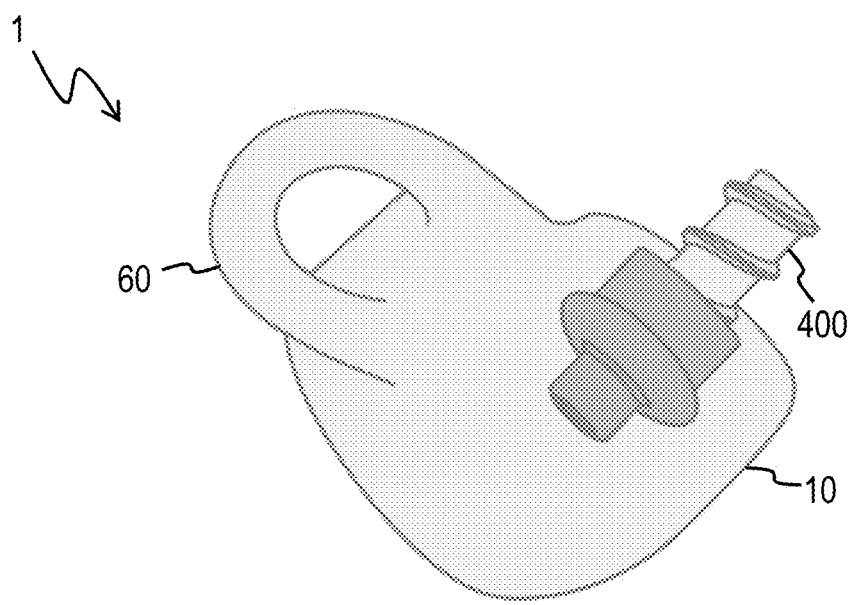
Figure 16A:
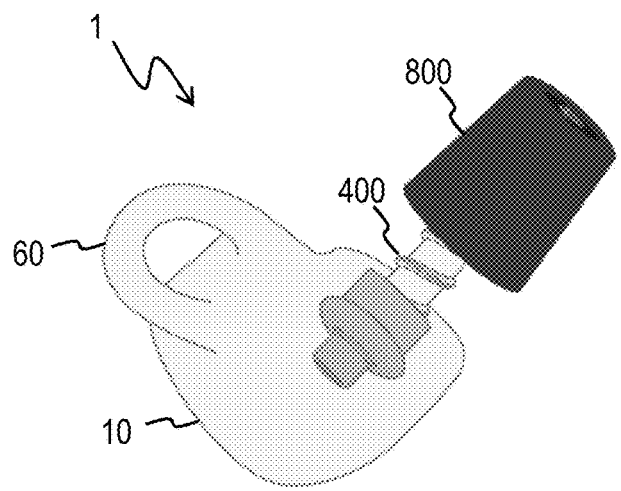
FIGS. 16A, 16B, 17A, and 17B are schematics showing mounting of various eartips onto an adapter insert in the body portion of a customizable hearing protection device.
Figure 16B:
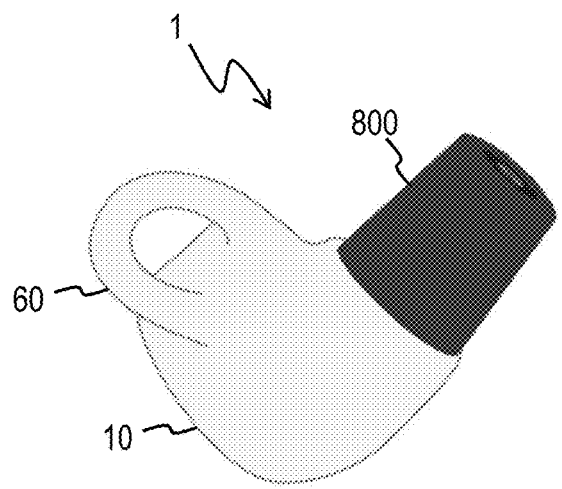
Figure 17A:
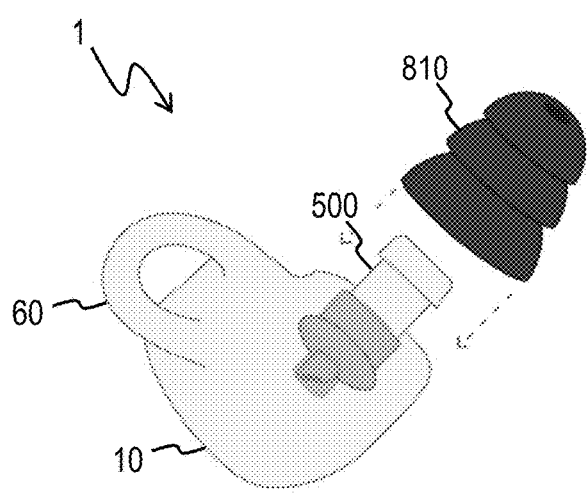
Figure 17B:
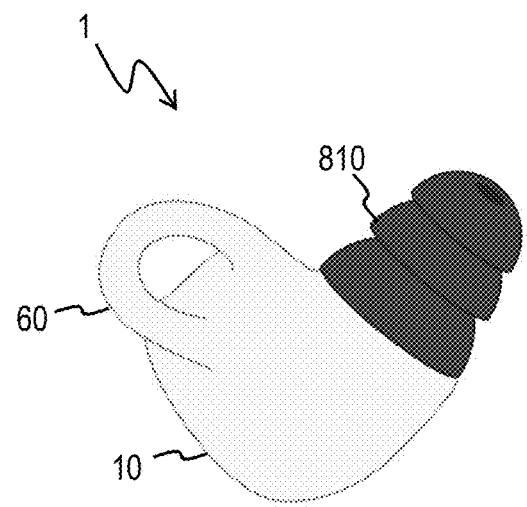

Referring to FIGS. 11A and 11B, the threaded noise reduction adapter insert 400 is especially well suited for noise reduction, to generally reduce the amount of sound coming into the ear. The threaded noise reduction adapter insert 400 includes a neck portion 450, a retention ridge 455, a stem portion 460 having threads 465, and a protuberance 410. A sound path 420 is defined inside the threaded noise reduction adapter insert 400 from an entrance end 430 of the threaded noise reduction adapter insert 400 to an exit end 440 of the threaded noise reduction adapter insert 400. The retention ridge 455 is configured to engage the insert grasping portion 45 of the inner portion 40 of the channel 20 of the body portion 10 (see FIGS. 4 and 5, for example), thereby preventing dislodging of the threaded noise reduction adapter insert 400 while the customizable hearing protection device 1 is inserted into the ear. The stem portion 460 having threads 465 is configured to stably hold a threaded eartip. The sound path 420 includes a curvature, by which the sound path 420 is not strictly horizontal but begins in a slightly downward orientation and bends to an essentially horizontal orientation. When the threaded noise reduction adapter insert 400 is in the body portion 10 of the customizable hearing protection device 1, the protuberance 410 is disposed within the middle portion 50 of the channel 20 of the body portion 10. The protuberance 410 is configured to enter into the sound modifying insert 200 (FIGS. 7A-7G), 201 (FIGS. 9A and 9B), 950 (FIG. 21A), such that pressure of the sound modifying device surrounding the protuberance 410 provides a greater seal and, thereby, a greater amount of noise reduction. FIGS. 15A and 15B are schematics illustrating the insertion of a threaded noise reduction adapter insert 400 into the body portion 10 of the customizable hearing protection device 1. FIGS. 16A and 16B are schematics illustrating the attachment of an eartip 800 to the threaded noise reduction adapter insert 400.

Figure 12A:
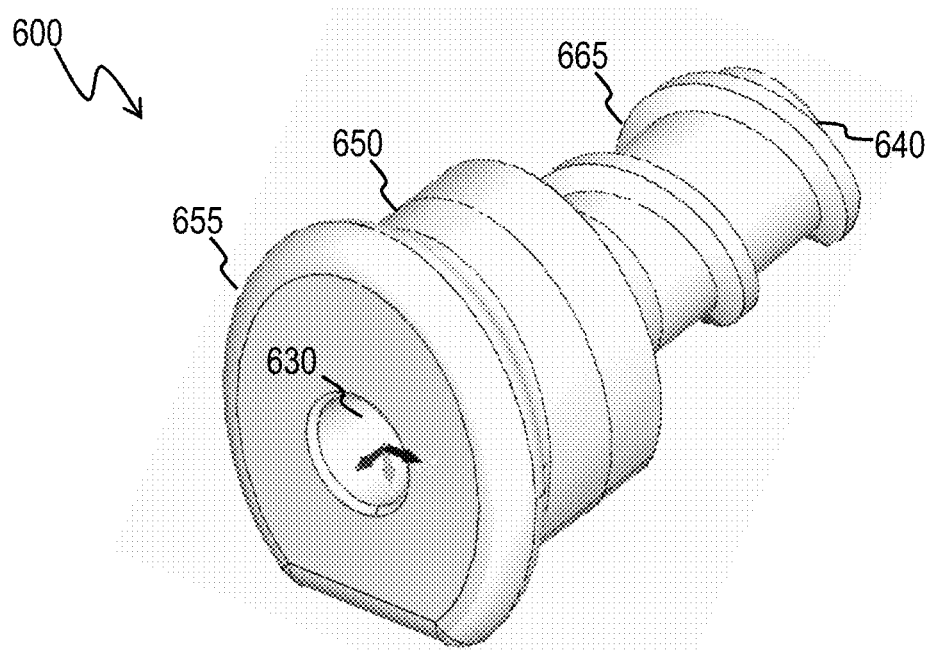
FIG. 12A is a side elevation of a threaded music adapter insert for a customizable hearing protection device.
Figure 12B:
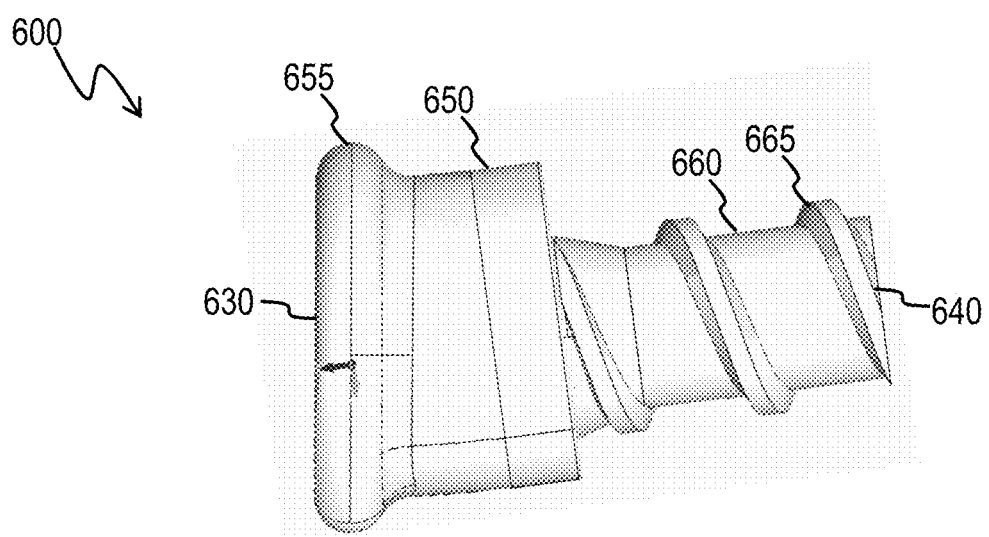
FIG. 12B is a side view of a threaded music adapter insert for a customizable hearing protection device.
Figure 13A:
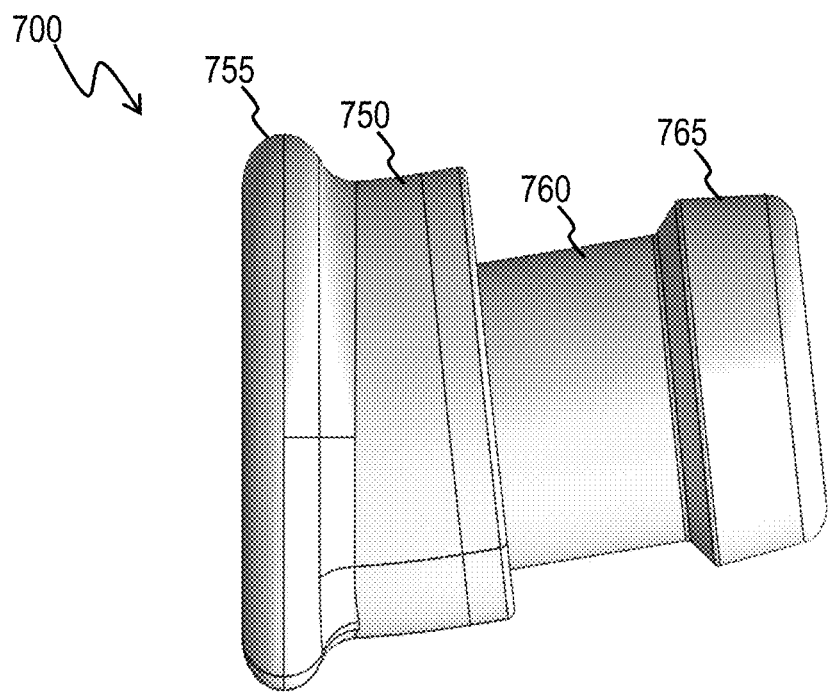
FIG. 13A is a side view of an interchangeable unthreaded music adapter insert for a customizable hearing protection device.
Figure 13B:
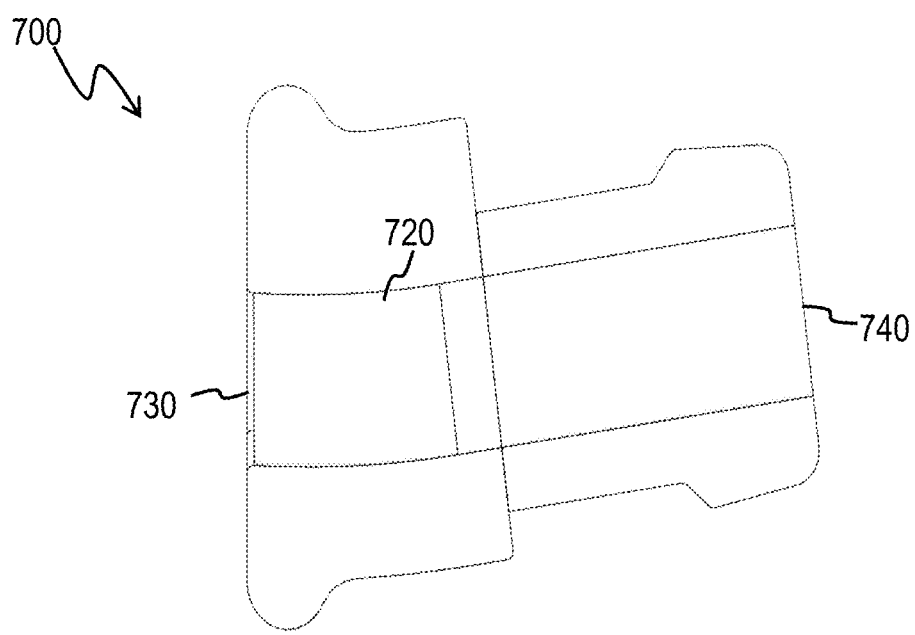
FIG. 13B is a cross-section of the interchangeable unthreaded music adapter insert of FIG. 13A.

Referring to FIGS. 12A and 12B, the threaded music adapter insert 600 is well suited for listening to music, such as from a headphone but not necessarily from a loud concert, when privacy and high-quality sound are desirable but hearing protection from sounds louder than a safe decibel range are not anticipated. The threaded music adapter insert 600 includes a neck portion 650, a retention ridge 655, and a stem portion 660 having threads 665. The threaded music adapter insert 600 lacks a protuberance. A sound path is defined inside the threaded music adapter insert 600 from an entrance end 630 of the threaded music adapter insert 600 to an exit end 640 of the threaded music adapter insert 600. The retention ridge 655 is configured to engage the insert grasping portion 45 of the inner portion 40 of the channel 20 of the body portion 10, thereby preventing dislodging of the threaded music adapter insert 600 while the customizable hearing protection device 1 is inserted into the ear. The stem portion 660 having threads 665 is designed to stably hold a threaded eartip. The sound path 620 includes a curvature, by which the sound path 620 is not strictly horizontal but begins in a slightly downward orientation and bends to an essentially horizontal orientation.

Figure 14:
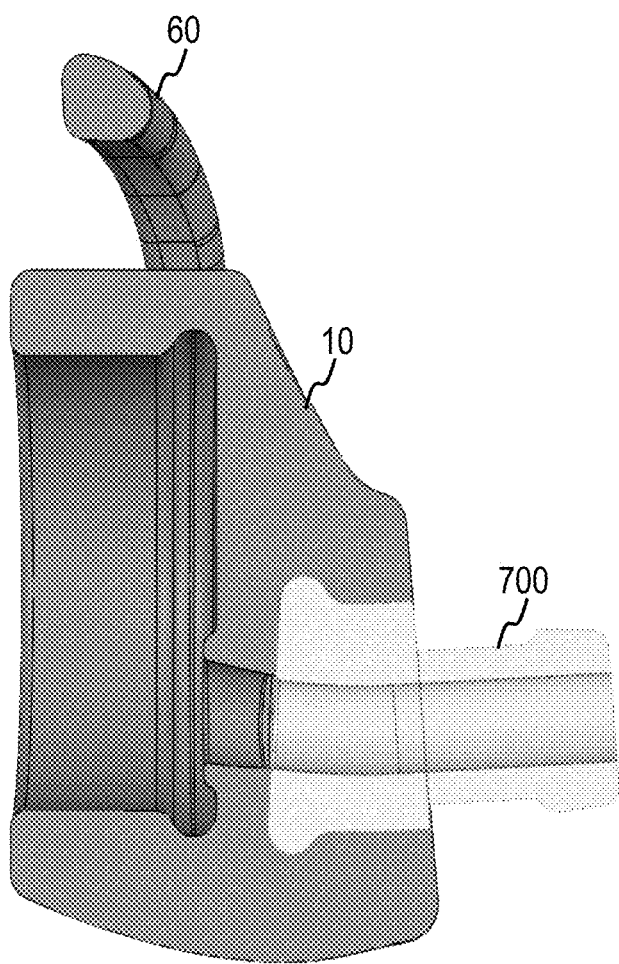
FIG. 14 is a cross-section of a customizable hearing protection device with an unthreaded music adapter insert.

Referring to FIGS. 13A and 13B, the unthreaded music adapter insert 700 also is well suited for listening to music, such as from a headphone but not necessarily from a loud concert, when privacy and high-quality sound are desirable but hearing protection from sounds louder than a safe decibel range are not anticipated. The unthreaded music adapter insert 700 includes a neck portion 750, a retention ridge 755, a stem portion 760, and a tip grasping portion 765. The unthreaded music adapter insert 700 lacks a protuberance. A sound path 720 is defined inside the unthreaded music adapter insert 700 from an entrance end 730 of the unthreaded music adapter insert 700 an exit end 740 of the unthreaded music adapter insert 700. The retention ridge 755 is configured to engage the insert grasping portion 45 of the inner portion 40 of the channel 20 of the body portion 10 (see FIGS. 4 and 14), thereby preventing dislodging of the unthreaded music adapter insert 700 while the customizable hearing protection device 1 is inserted into the ear. The tip grasping portion 765 is designed to stably hold an eartip. The sound path 720 includes a curvature, by which the sound path 720 is not strictly horizontal but begins in a slightly downward orientation and bends to an essentially horizontal orientation.

In one example embodiment of the customizable hearing protection device 1, the sound modifying insert is an adjustable noise-reduction attachment 200 as previously described, in which the adjustable noise-reduction attachment 200 includes a rotatable body 220 that is rotatable within the outer portion 30 of the channel 20 and in which the rotatable body 220 has a solid center portion 250 with a thickness that varies with respect to an angle of rotation of the rotatable body 220, whereby rotation of the rotatable body 220 causes a variable thickness of the solid center portion 250 to block entrance of sound into the sound path of the adapter insert. In such devices, the adapter insert includes a protuberance, disposed within the middle portion 50 of the channel 20, and the solid center portion 250 presses against the protuberance with a pressure proportional to the thickness of the solid center portion 250 blocking the entrance of sound into the sound path of the adapter insert. Such devices may further include a loop portion 60 defined in the body portion 10 and an interchangeable chip 100 removably inserted into the loop portion 60, the interchangeable chip 100 having an outer surface 150 with customized indicia 110 thereon.

As previously described according to embodiments, the hearing protection device may be configured to accept an interchangeable adapter insert and an interchangeable noise-reduction filter. The interchangeable noise reduction filter allows a user to adjust the reduction of variable hazardous noise entering the ear canal. Rotating the interchangeable noise reduction filter over the sound port opening in the silicone earplug produces a reduction of sound entering the ear canal. However, rotation of the interchangeable noise reduction filter over only the opening in the silicone earplug without the protuberance on the interchangeable threaded adapter insert produces a noise reduction rating (NRR) of approximately 9 to 11 decibels.

It is difficult to manufacture a device for variable noise reduction that is easy to manipulate by the customer especially while the product is in the ear and provides a higher (24 dB) certified NRR. The dilemma for adjustable noise reduction earplugs is the need to have a significant seal over the sound port opening, while still allowing effortless adjustability of the noise reducing mechanism when the device is in the ear.

The difficulty regarding reducing sound and allowing for a higher (24 dB) NRR with a rotational device involves creating a tight closure over the opening in the sound port. In particular, the better or tighter the seal around the rotational/movable part of the device that reduces noise, the harder it is to move the rotational part of the device to cover the sound port opening. To address this issue, the adapter inserts include a flat area to facilitate rotational movement of the sound reducing mechanism. The hearing protection device itself relies on rotation of material over the sound opening, increasing the downward pressure of the material over the sound port opening using a device that is easy for the customer to rotate while in the ear. The protuberance on the interchangeable threaded adapter insert provides an enhancement that increases the NRR from about 9-11 dB to 24 dB.

Furthermore, the actual design of the interchangeable adapter inserts makes it more difficult to remove the adapter when pulling them directly (0 degree) from the earplugs. This allows the product to pass force testing, meaning the device can be removed from the ear canal at 0 degrees and 45 degrees without the attached foam eartip remaining in the ear canal. It also does not allow the adapter insert to rotate in a circle while embedded in the silicone earplug. However, the adapter insert design allows for easy removal from the silicone earplug by applying pressure at a downward angle to the adapter insert.

The hearing protection devices of this disclosure possess additional distinct advantages. First, they are easy to rotate, providing a variable interchangeable noise reduction filter beyond a traditional "Open/Close" option. Second, they have lower starting sound reduction and higher certified NRR than other adjustable earplugs in the industry. Third, they have numerous interchangeable noise reduction and sound manipulation accessories.

Conventional hearing protection products may advertise an average noise reduction, however this is NOT the actual NRR. They may advertise a 30 dB noise reduction, but not a NRR. In addition, products that offer a higher NRR using an open and close method, have a higher starting NRR (in the open position) before customers activate the technology and close the opening over the sound port. Other products may advertise a high decibel reduction based on a single frequency or may advertise an average noise reduction. However, measurements such as average attenuation are not equivalent to a certified NRR. The NRR testing evaluates lower frequencies such as 125 Hz into the overall calculations of the certified rating. Numerous products can significantly decrease the high frequency energy, but fall short in regards to decreasing the low frequency sounds. In order to decrease the low frequency region, the product must have a consistent tight seal over the sound port opening.

The hearing protection devices according to embodiments herein enables effortless sound reduction manipulations through contact with the protuberance on the interchangeable threaded adapter inserts. In addition, the protuberance on the interchangeable high-fidelity adapter inserts enable for consistent flat response for music. Again, the protuberance on the high-fidelity adapter insert is the only way the hearing protection device can transition into a certified high-fidelity music earplug.

The High-Fidelity Music Filters described herein function differently. Simplistically, the human ear is designed to increase certain high frequencies. When a person plugs an ear with a customary earplug, they eliminate the "Natural Ear Canal Resonance" of sound, especially in these high frequency regions. To achieve a linear attenuation of sound traveling to the hearing organ, the product must account for several items including, but not limited to the length, volume, curvature, and diameter of the opening in the sound port. Linear attenuation is correlated with more natural hearing when using passive hearing protection.

The Linear Attenuation High-Fidelity Music Filters described herein are appropriate for use by musicians, music lovers, and concert goers and anywhere communication in noise is essential. The filters provide a tuned, essentially flat attenuation response over the entire frequency range. The natural sound of live concert music will be maintained, but at a safer, lower level. These filters provide the needed sound attenuation for all music listeners or performers, but also satisfy the most discerning audiophiles. They are also beneficial for preserving speech in noisy environments such as restaurants, night clubs, festivals, and public transportation.

Further embodiments are directed to kits for assembling a customizable hearing protection device according to embodiments herein from components of the customizable hearing protection device as described herein. The kits may include at least one body portion; a sound modifying insert selected from an adjustable noise-reduction attachment, a speaker, a high-fidelity music cartridge insert, or a combination thereof; at least one adapter insert; and at least one eartip. In some embodiments of the kits, the body portion comprises a loop portion defined in the body portion, and the kit further includes at least one interchangeable chip operable to be inserted in the loop portion. The at least one interchangeable chip may include an outer surface having customized indicia thereon. In some embodiments, the at least one body portion includes a first body portion configured for use in a left ear of a wearer and a second body portion configured for use in a right ear of a wearer.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue. The term "substantially" is used herein also to represent the degree by which a quantitative representation may vary from a stated reference without resulting in a change in the basic function of the subject matter at issue. Thus, it is used to represent the inherent degree of uncertainty that may be attributed to any quantitative comparison, value, measurement, or other representation, referring to an arrangement of elements or features that, while in theory would be expected to exhibit exact correspondence or behavior, may in practice embody something less than exact.

Unless otherwise defined, all technical and scientific terms used herein have the same meaning as commonly understood by one of ordinary skill in the art to which the invention belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

As used herein, the terms "horizontal" and "vertical" are relative terms only, are indicative of a general relative orientation only, and do not necessarily indicate perpendicularity. These terms also may be used for convenience to refer to orientations used in the figures, which orientations are used as a matter of convention only and are not intended as characteristic of the devices shown. The present invention and the embodiments thereof to be described herein may be used in any desired orientation. Moreover, horizontal and vertical walls need generally only be intersecting walls, and need not be perpendicular. Similarly, though directional terms such as "above," "below," "top," and "bottom" may be used with reference to various figures to describe relative orientations in the figures, these and other such relative terms should not be interpreted to mean that only one orientation is possible in practice or as part of any particular embodiment.

It is noted that one or more of the following claims utilize the term "wherein" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

It should be understood that where a first component is described as "comprising" or "including" a second component, it is contemplated that, in some embodiments, the first component "consists" or "consists essentially of" the second component. Additionally, the term "consisting essentially of" is used in this disclosure to refer to quantitative values that do not materially affect the basic and novel characteristic(s) of the disclosure.

It should be understood that any two quantitative values assigned to a property or measurement may constitute a range of that property or measurement, and all combinations of ranges formed from all stated quantitative values of a given property or measurement are contemplated in this disclosure.

While particular embodiments have been illustrated and described herein, it should be understood that various other changes and modifications may be made without departing from scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A customizable hearing protection device, comprising:
   a body portion;
   a channel defined through the body portion from a distal side of the body portion to a proximal side of the body portion opposite the distal side;
   a sound modifying insert removably inserted into an outer portion of the channel adjacent to the distal side of the body portion, the outer portion having a first diameter;
   an adapter insert removably inserted into an inner portion of the channel adjacent to the proximal side of the body portion, the inner portion having a second diameter, the second diameter being less than the first diameter; and
   an eartip mounted to a mounting portion of the adapter insert that protrudes from the proximal side of the body portion;
   wherein:
   the channel comprises a middle portion connecting the outer portion and the inner portion, the middle portion having a third diameter, the third diameter being less than the second diameter;
   the adapter insert has a sound path defined through the adapter insert from an entrance end of the adapter insert to an exit end of the adapter insert;
   the outer portion of the channel comprises a first main portion with the first diameter, and an accessory grasping portion with a fourth diameter, the fourth diameter being greater than the first diameter; and the inner portion of the channel comprises a second main portion with the second diameter and an insert grasping portion with a fifth diameter, the fifth diameter being greater than the second diameter.

2. The customizable hearing protection device of claim 1, wherein the body portion further comprises:
   a loop portion defined in the body portion; and
   an interchangeable chip removably inserted into the loop portion.

3. The customizable hearing protection device of claim 2, wherein the interchangeable chip comprises:
   a bottom surface that conforms to a surface of the body portion;
   a top groove that engages the loop portion of the body portion.

4. The customizable hearing protection device of claim 3, wherein the interchangeable chip further comprises an outer surface having customized indicia thereon.

5. The customizable hearing protection device of claim 1, wherein:
   the body portion further comprises a loop portion defined in the body portion and an interchangeable chip removably inserted into the loop portion, the interchangeable chip comprising an outer surface having customized indicia thereon;
   the sound modifying insert is selected from an adjustable noise-reduction attachment, a speaker, or a high-fidelity music cartridge insert; and
   the adapter insert comprises a protuberance, the protuberance being disposed within the middle portion of the channel.

6. The customizable hearing protection device of claim 1, wherein the sound path of the adapter insert is curved.

7. The customizable hearing protection device of claim 1, wherein the sound modifying insert is selected from an adjustable noise-reduction attachment, a speaker, or a high-fidelity music cartridge insert.

8. The customizable hearing protection device of claim 7, wherein the sound modifying insert is an adjustable noise-reduction attachment, the adjustable noise-reduction attachment comprising a rotatable body that is rotatable within the outer portion of the channel, the rotatable body having a solid center portion with a thickness that varies with respect to an angle of rotation of the rotatable body, whereby rotation of the rotatable body causes a variable thickness of the solid center portion to block entrance of sound into the sound path of the adapter insert.

9. The customizable hearing protection device of claim 1, wherein the adapter insert comprises a protuberance, the protuberance being disposed within the middle portion of the channel.

10. A kit for assembling a customizable hearing protection device according to claim 1, the kit comprising:
    at least one body portion;
    a sound modifying insert selected from an adjustable noise-reduction attachment, a speaker, a high-fidelity music cartridge insert, or a combination thereof;
    at least one adapter insert;
    at least one eartip.

11. The kit of claim 10, wherein the body portion comprises a loop portion defined in the body portion, the kit further comprising at least one interchangeable chip operable to be inserted in the loop portion, the at least one interchangeable chip comprising an outer surface having customized indicia thereon.

12. The kit of claim 10, wherein the at least one body portion comprises a first body portion configured for use in a left ear of a wearer and a second body portion configured for use in a right ear of a wearer.

13. The customizable hearing protection device of claim 1, wherein the sound modifying insert comprises a rocker switch, the rocker switch having:
    an open state in which sound passes through the customizable hearing protection device unattenuated; and
    a closed state in which maximum sound attenuation is activated for the customizable hearing protection device.

14. The customizable hearing protection device of claim 13, wherein the rocker switch is an assembly, the assembly comprising:
    a switch shell comprising a retention ridge configured to retain the rocker switch by friction fit in the outer portion of the channel of the body portion; and
    a rocking component tiltably mounted inside the switch shell.

15. The customizable hearing protection device of claim 14, wherein the rocking component comprises:
    a rocker body;
    a press plate on one end of the rocker body, the press plate having an opening end, a closing end, and a sound hole defined therein;
    a muffling pad on a side of the rocking component opposite the press plate.

16. The customizable hearing protection device of claim 15, wherein the rocking component is seated inside the switch shell so that a rim space remains open underneath or behind the rocking component and inside the retention ridge.

17. The customizable hearing protection device of claim 16, wherein:
    the rocker switch is inserted into the outer portion of the channel of the body portion;
    the muffling pad is oriented to face the middle portion of the channel;
    in the open state of the rocker switch, sound waves from ambient environment enter through the sound hole, pass through the rocker switch to reach the rim space, then deflect into the middle portion of the channel;
    in the closed state of the rocker switch, the muffling pad is firmly pressed over the an opening to the middle portion of the channel, whereby sound waves from ambient environment enter through the sound hole, pass through the rocker switch to reach the rim space, then are prevented from reaching the middle portion of the channel.

18. The customizable hearing protection device of claim 14, wherein the switch shell comprises inner ribs to lock the rocking component into either the open state or the closed state.

19. The customizable hearing protection device of claim 14, wherein the switch shell further comprises swivel holes into which side pins of the rocking component are mounted.

20. A customizable hearing protection device, comprising:
    a body portion;
    a channel defined through the body portion from a distal side of the body portion to a proximal side of the body portion opposite the distal side;
    a sound modifying insert removably inserted into an outer portion of the channel adjacent to the distal side of the body portion, the outer portion having a first diameter;
    an adapter insert removably inserted into an inner portion of the channel adjacent to the proximal side of the body portion, the inner portion having a second diameter, the second diameter being less than the first diameter; and an eartip mounted to a mounting portion of the adapter insert that protrudes from the proximal side of the body portion;

wherein:

the channel comprises a middle portion connecting the outer portion and the inner portion, the middle portion having a third diameter, the third diameter being less than the second diameter;

the adapter insert has a sound path defined through the adapter insert from an entrance end of the adapter insert to an exit end of the adapter insert, wherein the sound modifying insert is an adjustable noise-reduction attachment;

the adjustable noise-reduction attachment comprises a rotatable body that is rotatable within the outer portion of the channel;

the rotatable body has a solid center portion with a thickness that varies with respect to an angle of rotation of the rotatable body, whereby rotation of the rotatable body causes a variable thickness of the solid center portion to block entrance of sound into the sound path of the adapter insert;

the adapter insert comprises a protuberance, the protuberance being disposed within the middle portion of the channel; and the solid center portion presses against the protuberance with a pressure proportional to the thickness of the solid center portion blocking the entrance of sound into the sound path of the adapter insert.

* * * * *